(12) United States Patent
Southard et al.

(10) Patent No.: US 11,413,018 B2
(45) Date of Patent: Aug. 16, 2022

(54) ULTRASOUND FINGER PROBE

(71) Applicant: Bard Access Systems, Inc., Salt Lake City, UT (US)

(72) Inventors: Jeanette E. Southard, Park City, UT (US); Matthew J. Prince, West Jordan, UT (US); Tab Robbins, Layton, UT (US); Timothy L. Creamer, Ocean Springs, MS (US); Kent F. Beck, Layton, UT (US); Paul T. Westwood, Kaysville, UT (US); Andrew J. Lengyel, Sandy, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 743 days.

(21) Appl. No.: 16/130,756

(22) Filed: Sep. 13, 2018

(65) Prior Publication Data

US 2019/0076121 A1    Mar. 14, 2019

Related U.S. Application Data

(60) Provisional application No. 62/558,234, filed on Sep. 13, 2017.

(51) Int. Cl.
*A61B 8/00* (2006.01)
*A61B 8/12* (2006.01)

(52) U.S. Cl.
CPC .............. *A61B 8/4455* (2013.01); *A61B 8/12* (2013.01); *A61B 8/4254* (2013.01); *A61B 8/4427* (2013.01); *A61B 8/54* (2013.01)

(58) Field of Classification Search
CPC ....... A61B 8/4455; A61B 8/4427; A61B 8/12; A61B 8/54; A61B 8/4254; A61B 5/6826; A61B 2017/00438
See application file for complete search history.

(56) References Cited

U.S. PATENT DOCUMENTS 4,545,386 A    10/1985 Hetz et al.
4,869,260 A    9/1989 Young et al.
(Continued)

FOREIGN PATENT DOCUMENTS

WO    17019873 A1    2/2017

OTHER PUBLICATIONS

Fukuda Denshi, UF-760AG Specification sheet. 2014.
(Continued)

*Primary Examiner* — Rochelle D Turchen
(74) *Attorney, Agent, or Firm* — Rutan & Tucker LLP

(57) ABSTRACT

An ultrasound probe ("probe") for use with an ultrasound imaging system is disclosed. In particular, the probe is sized and configured so as to be supported and readily used with as little as one finger on a single hand of a user of the imaging system. This configuration enables remaining fingers on the hand of the user to be employed for other purposes, such as skin traction and patient contact. In one embodiment, therefore, an ultrasound probe is disclosed, comprising a body, a lens included on head portion of the body, a stabilizing portion extending from the body and configured to stabilize the body on a skin surface of a patient without user assistance, and a finger grip portion configured to enable a user of the probe to grasp and maneuver the probe during use thereof with no more than two fingers on a single hand of the user.

19 Claims, 17 Drawing Sheets

(56) References Cited

U.S. PATENT DOCUMENTS

| | | | |
|---|---|---|---|
| 4,898,177 A | 2/1990 | Takano et al. | |
| 5,088,500 A * | 2/1992 | Wedel | A61B 1/00142 |
| | | | 600/452 |
| 5,152,293 A | 10/1992 | Vonesh et al. | |
| 5,182,972 A | 2/1993 | Skaleski | |
| 5,195,519 A | 3/1993 | Angelsen | |
| 5,284,147 A | 2/1994 | Hanaoka et al. | |
| 5,598,846 A | 2/1997 | Peszynski | |
| 5,671,747 A | 9/1997 | Connor | |
| 5,752,517 A * | 5/1998 | Harman | A61B 8/42 |
| | | | 600/437 |
| 5,792,059 A | 8/1998 | Furia et al. | |
| 5,986,446 A | 11/1999 | Williamson | |
| 6,029,530 A | 2/2000 | Patton et al. | |
| 6,126,608 A | 10/2000 | Kemme et al. | |
| 6,193,709 B1 | 2/2001 | Miyawaki et al. | |
| 6,485,425 B2 | 11/2002 | Seward et al. | |
| 6,746,402 B2 | 6/2004 | Ustuner | |
| 7,037,270 B2 | 5/2006 | Seward | |
| 7,128,720 B2 | 10/2006 | Podany | |
| 7,297,115 B2 | 11/2007 | Bates et al. | |
| 8,118,747 B2 | 2/2012 | Furia et al. | |
| 8,211,026 B2 | 7/2012 | Schutz et al. | |
| 8,277,417 B2 | 10/2012 | Fedinec | |
| 8,827,909 B2 | 9/2014 | Kierulf et al. | |
| D743,040 S | 11/2015 | Corbett, III et al. | |
| 2004/0225217 A1 * | 11/2004 | Voegele | A61B 8/42 |
| | | | 600/439 |
| 2005/0085731 A1 | 4/2005 | Miller et al. | |
| 2005/0096554 A1 | 5/2005 | Dudik et al. | |
| 2006/0025690 A1 | 2/2006 | Guigne et al. | |
| 2006/0173331 A1 | 8/2006 | Booton et al. | |
| 2008/0146936 A1 * | 6/2008 | Furia | A61B 8/4455 |
| | | | 600/459 |
| 2008/0306387 A1 | 12/2008 | Schutz et al. | |
| 2009/0137905 A1 | 5/2009 | Watson et al. | |
| 2009/0163807 A1 | 6/2009 | Sliwa | |
| 2010/0256461 A1 | 10/2010 | Mohamedali et al. | |
| 2010/0305447 A1 | 12/2010 | Dudik et al. | |
| 2011/0105908 A1 | 5/2011 | Schutz et al. | |
| 2011/0137176 A1 | 6/2011 | Miller et al. | |
| 2012/0197131 A1 | 8/2012 | Georgiev et al. | |
| 2013/0085325 A1 | 4/2013 | Fuller et al. | |
| 2013/0085394 A1 | 4/2013 | Corbett, III et al. | |
| 2013/0158365 A1 | 6/2013 | Chey et al. | |
| 2013/0237819 A1 | 9/2013 | Sun et al. | |
| 2013/0261465 A1 | 10/2013 | Nakamura et al. | |
| 2014/0200445 A1 | 7/2014 | Boezaart et al. | |
| 2014/0330087 A1 | 11/2014 | Succi et al. | |
| 2015/0182189 A1 | 7/2015 | Mullen | |
| 2015/0257733 A1 | 9/2015 | Corbett, III et al. | |
| 2016/0119529 A1 | 4/2016 | Stolka et al. | |
| 2018/0153504 A1 * | 6/2018 | Herickhoff | A61B 8/085 |
| 2018/0193098 A1 * | 7/2018 | Caluser | A61B 34/20 |

OTHER PUBLICATIONS www.sonivate.com, last accessed Sep. 3, 2019.
PCT/US2018/050925 filed Sep. 13, 2018 International Search Report and Written Opinion filed Dec. 7, 2018.

* cited by examiner

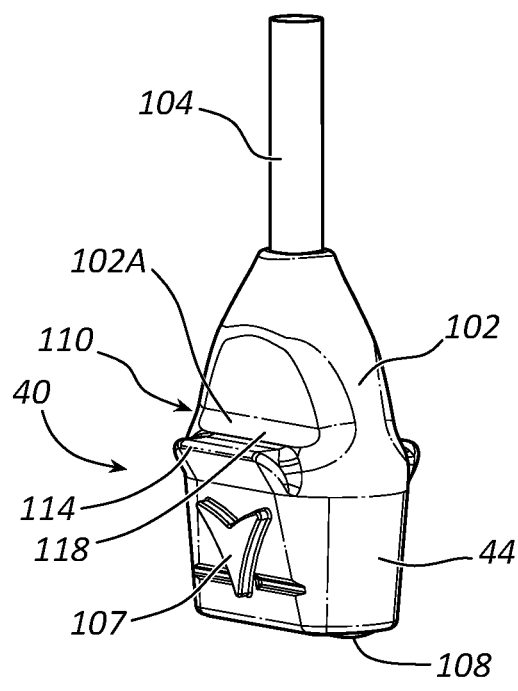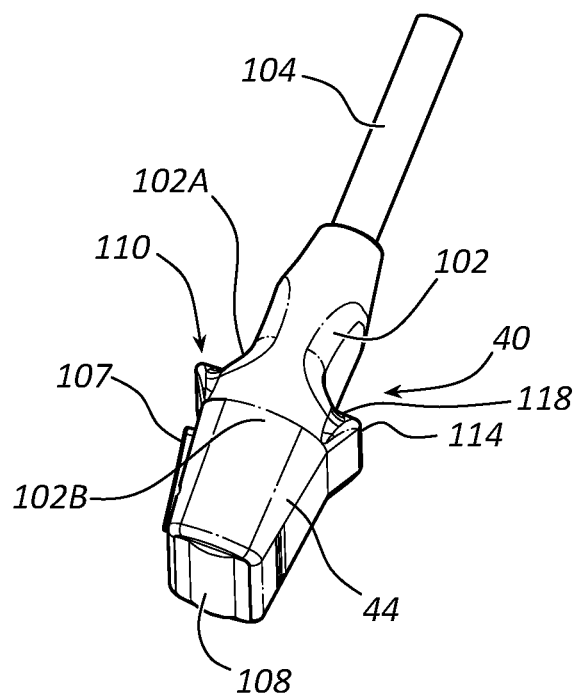
FIG. 3A　　　　FIG. 3B
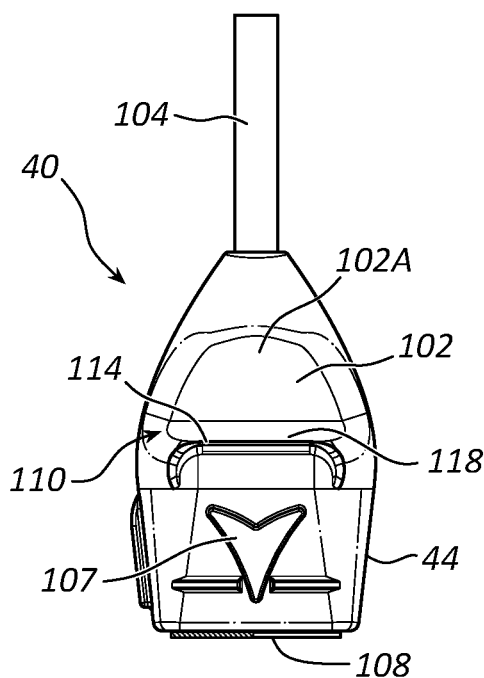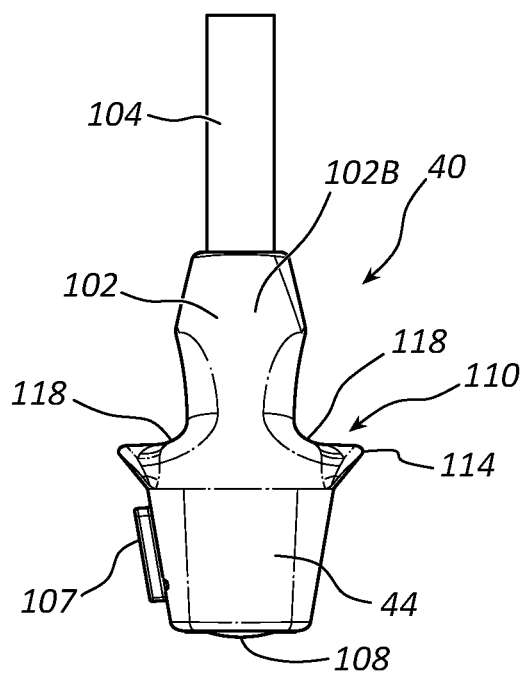
FIG. 3C　　　　FIG. 3D

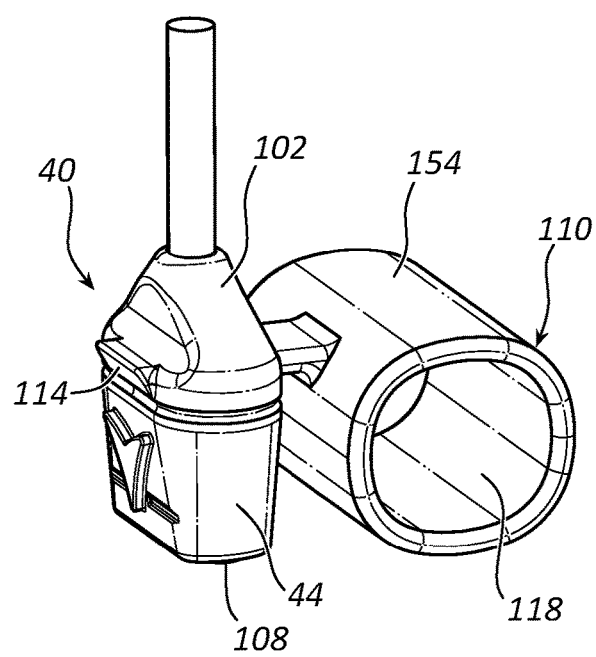
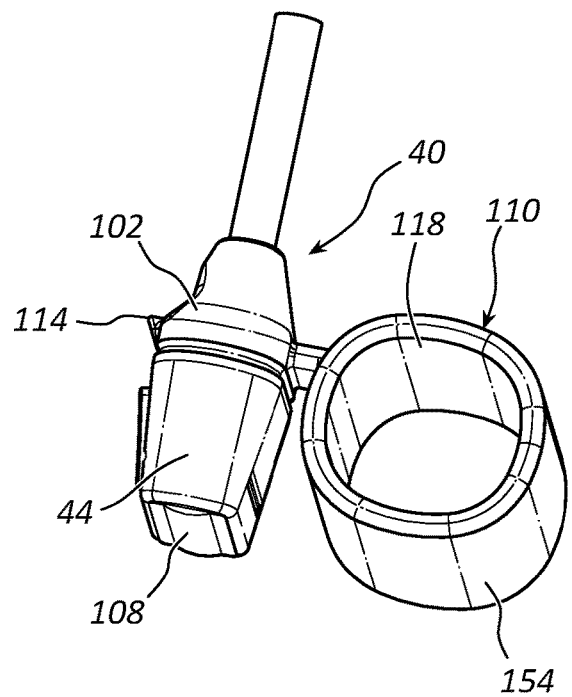
FIG. 7A  FIG. 7B
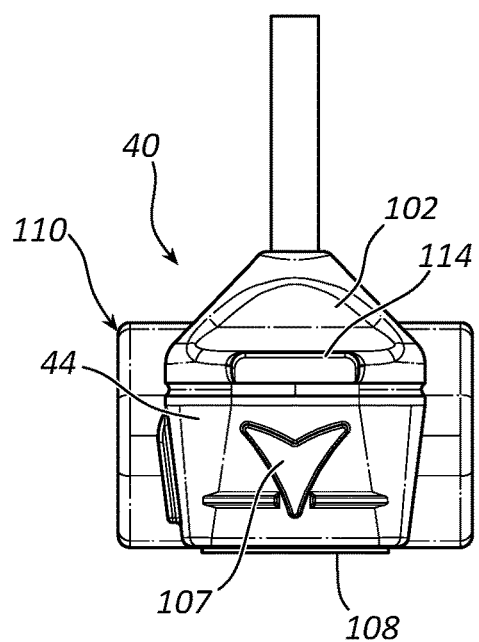
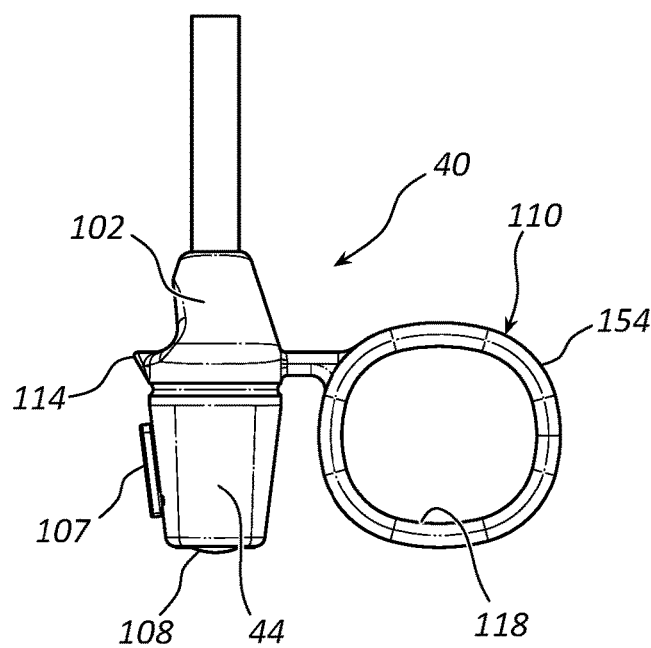
FIG. 7C  FIG. 7D

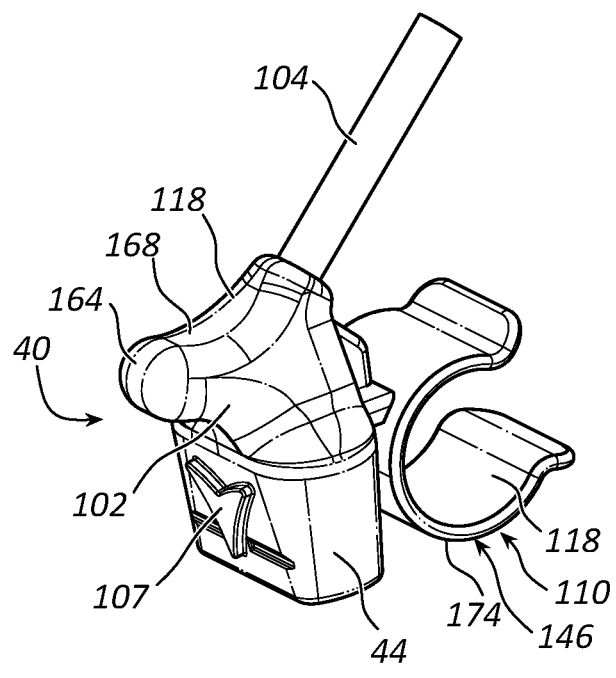 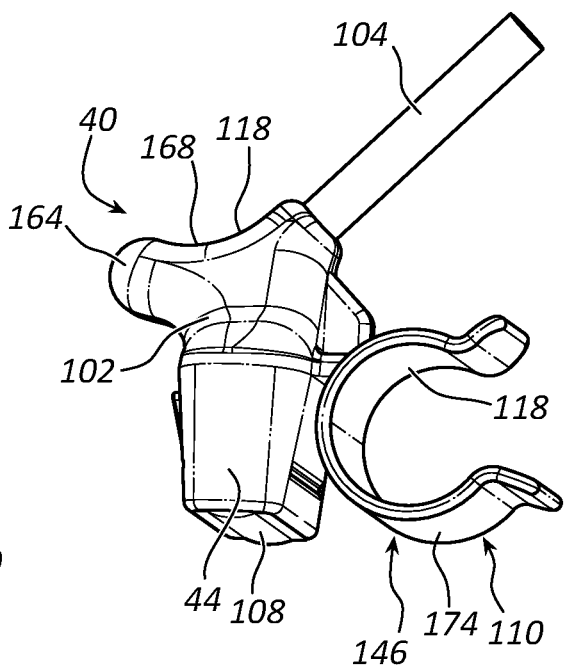
FIG. 11A     FIG. 11B
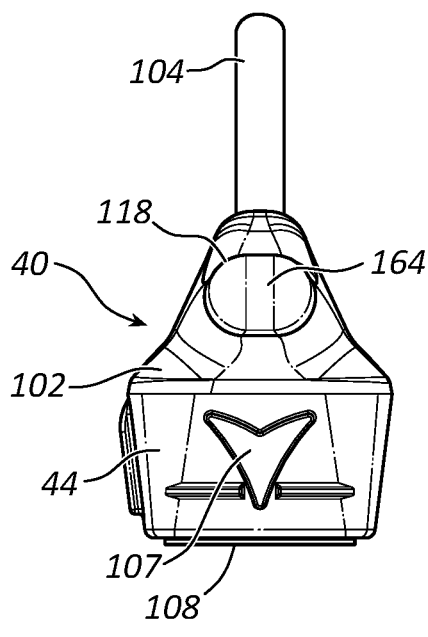 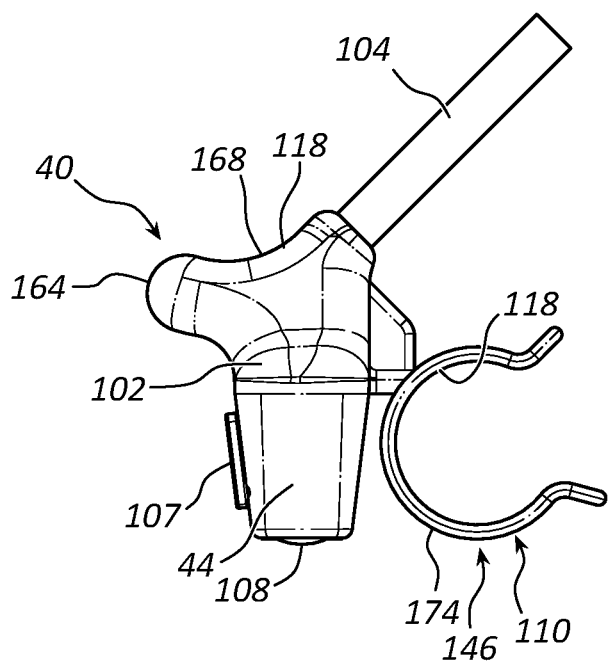
FIG. 11C     FIG. 11D

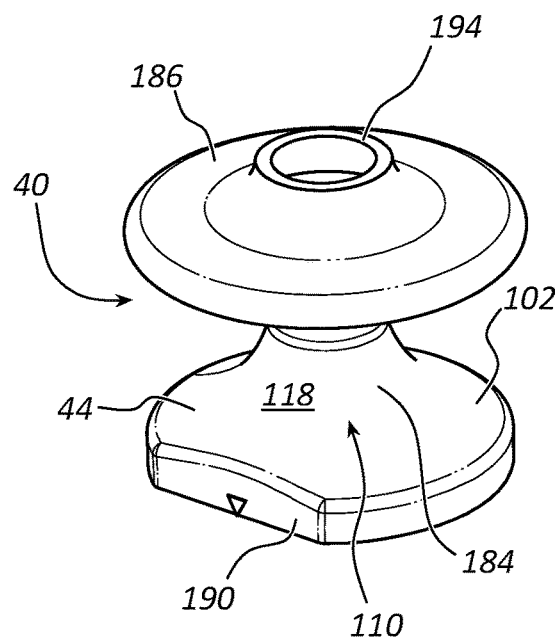
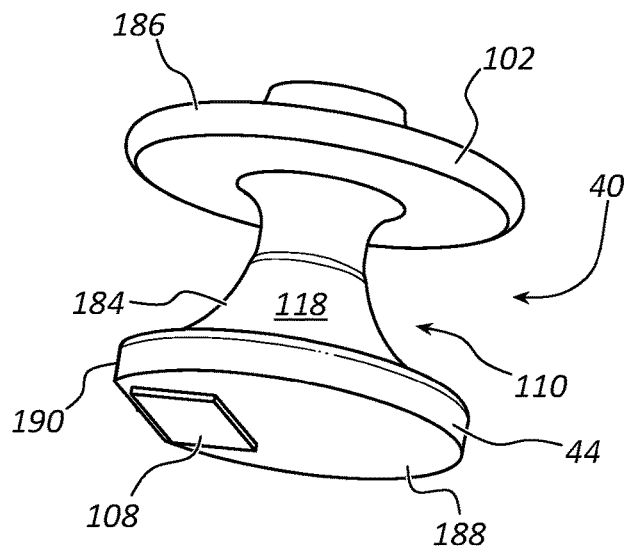
FIG. 13A  FIG. 13B
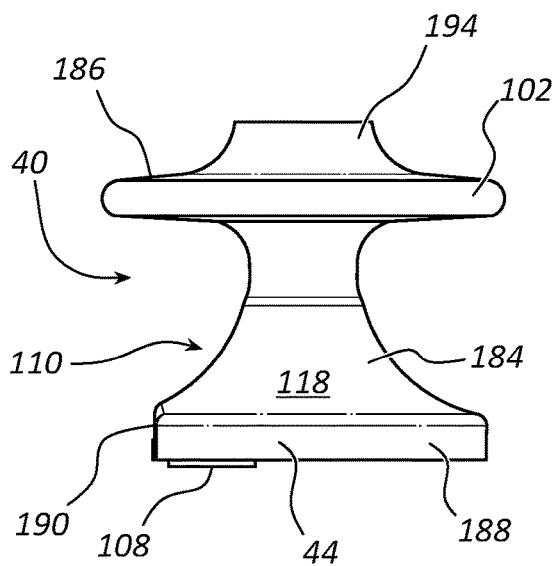
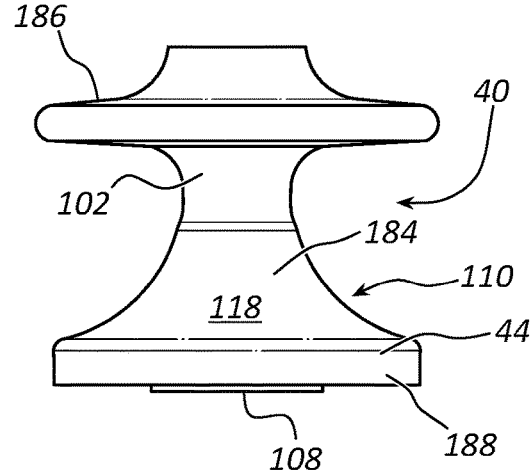
FIG. 13C  FIG. 13D

ULTRASOUND FINGER PROBE

CROSS-REFERENCE TO RELATED APPLICATIONS

This application claims the benefit of U.S. Provisional Patent Application No. 62/558,234, filed Sep. 13, 2017, and entitled "Ultrasound Finger Probe," which is incorporated herein by reference in its entirety.

BRIEF SUMMARY

Briefly summarized, embodiments of the present invention are directed to an ultrasound probe ("probe") for use with an ultrasound imaging system. In particular, the probe is sized and configured so as to be supported and readily used with as little as one finger on a single hand of a user of the imaging system, such as a clinician. This configuration enables remaining fingers on the hand of the user to be employed for other purposes, including applying traction to the skin surface of the patient proximate the imaging site and providing touch comfort to the patient. With it supported by as little as a single finger, the probe can easily be positioned by the user in a proper orientation against the skin surface during imaging procedures.

Further, the probe is configured in one embodiment to enable the user's hand to be positioned substantially horizontally with respect to (parallel to) the skin surface of the patient, thus enabling relatively accurate probe positioning (e.g., lifting, placing, pressing, etc.) and scanning operations to be performed.

In one embodiment, the probe also includes a stabilizing portion to assist in maintaining stability of the probe while on the skin surface.

In one embodiment, therefore, an ultrasound probe is disclosed, comprising a body, a lens included on head portion of the body through which ultrasound signals can be passed, a stabilizing portion extending from the body and configured to stabilize the body on a skin surface of a patient without user assistance, and a finger grip portion configured to enable a user of the probe to grasp and maneuver the probe during use thereof with no more than two fingers on a single hand of the user.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A-3D are various views of an ultrasound probe according to one embodiment;

FIGS. 7A-7D are various views of an ultrasound probe according to one embodiment;

FIGS. 11A-11D are various views of an ultrasound probe according to one embodiment;

FIGS. 13A-13D are various views of an ultrasound probe according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an ultrasound probe ("probe") for use with an ultrasound imaging system. In particular, the probe is sized and configured so as to be supported and readily used with one or more fingers on a single hand of a user of the imaging system, such as a clinician. This configuration enables remaining fingers on the hand of the user to be employed for other purposes, including applying traction to the skin surface of the patient proximate the imaging site, providing touch comfort to the patient, etc. With it supported by as little as a single finger, the probe can easily be positioned by the user in a proper orientation against the skin surface during imaging procedures.

Further, the probe is configured in one embodiment to enable the user's hand to be positioned substantially horizontally with respect to (i.e., parallel to) the skin surface of the patient, thus enabling relatively accurate probe positioning (e.g., lifting, placing, pressing, etc.) and scanning operations to be performed.

In one embodiment, the probe also includes a stabilizing portion to assist in maintaining stability of the probe while on the skin surface.

In one embodiment, the probe is configured to be supported and manipulated by a single finger, with the finger positioned directly over a lens portion of the probe. Such a position enables the user to easily and accurately move the probe on the skin surface as to position the probe with subtle movements as desired.

Figure 1:
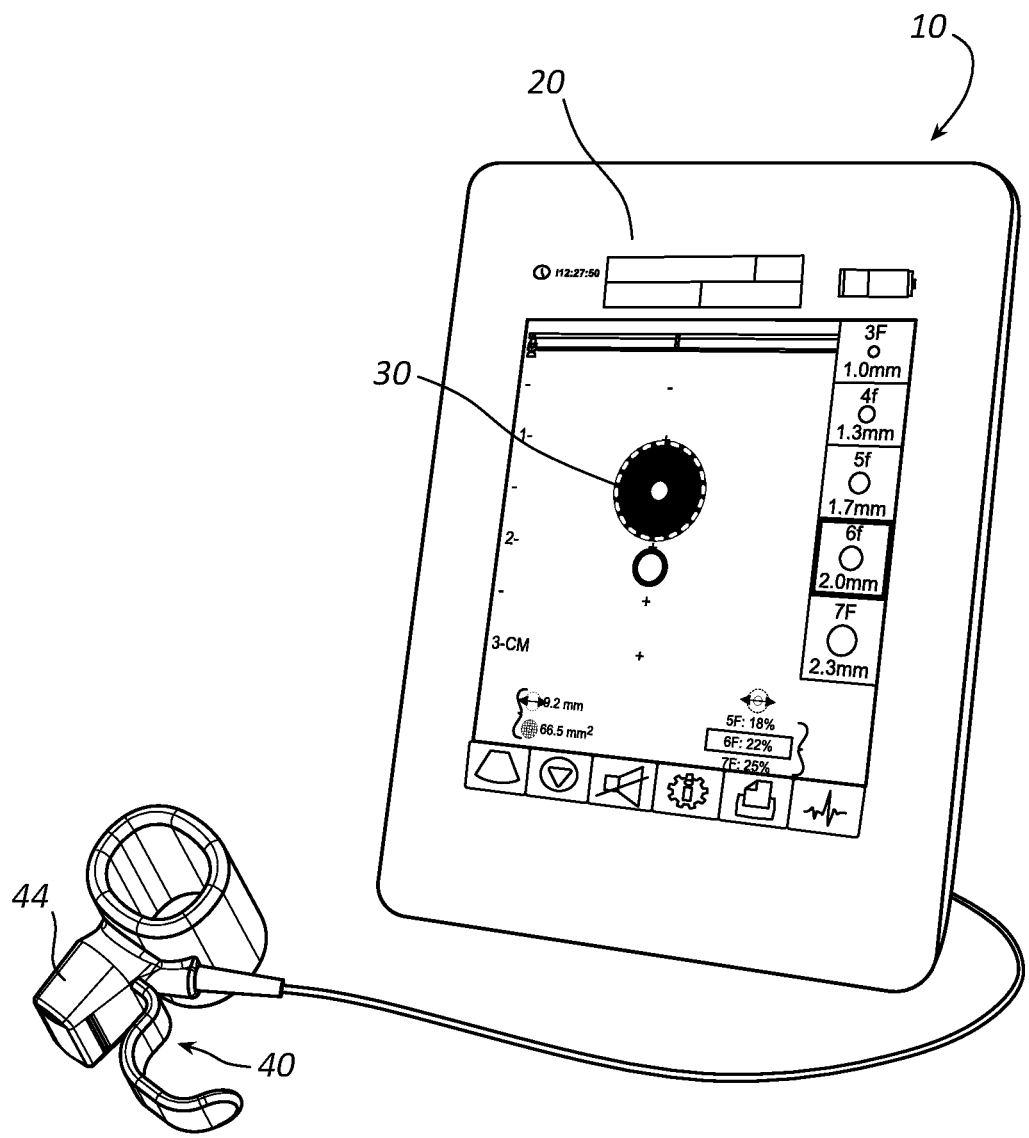
FIG. 1 is a perspective view of an ultrasound imaging system and included probe according to one embodiment.

FIG. 1 shows various components of an ultrasound imaging system 10 (also referred to herein as "imaging system" or "system"), according to one embodiment. As shown, the system 10 includes a console 20 housing various electronic and other components necessary for processing and depicting ultrasonic images. The console 20 includes a touchscreen display 30 for depicting ultrasonic images and for enabling touch-based input by a clinician to control the device and its functionality. An ultrasound probe ("probe") 40, containing one or more transducer elements in a head 44 thereof for emitting and receiving ultrasonic signals, is operably attached to the console 20 via a cable or other suitable interface, including wireless connectivity.

In one embodiment, an optional cap including a hydrogel insert can be removably attached to the head 44 of the probe 40 so as to cover a lens portion thereof. The hydrogel insert provides an ultrasonically transparent interface between the probe head 44 and the skin surface. A needle guide can also be included with the cap to assist with guiding needles through the patient's skin and into the vessel being imaged by the system 10. In another embodiment, the needle guide is included on the probe itself. Further details regarding the probe cap, hydrogel insert, and needle guide can be found in U.S. Pat. Nos. 10,639,008, filed Aug. 9, 2011, and titled "Support and Cover Structures for an Ultrasound Probe Head," and U.S. Pat. No. 9,788,812, filed Jun. 22, 2012, and titled "Needle Guide with Selectable Aspects." Each of the foregoing applications is incorporated herein by reference in its entirety. In yet another embodiment, a sheath or cover can be removably placed over the probe 40 to provide a sterile barrier. Note that other ultrasound imaging devices and systems that differ from that shown here can also benefit from the embodiments described herein.

Figure 2:
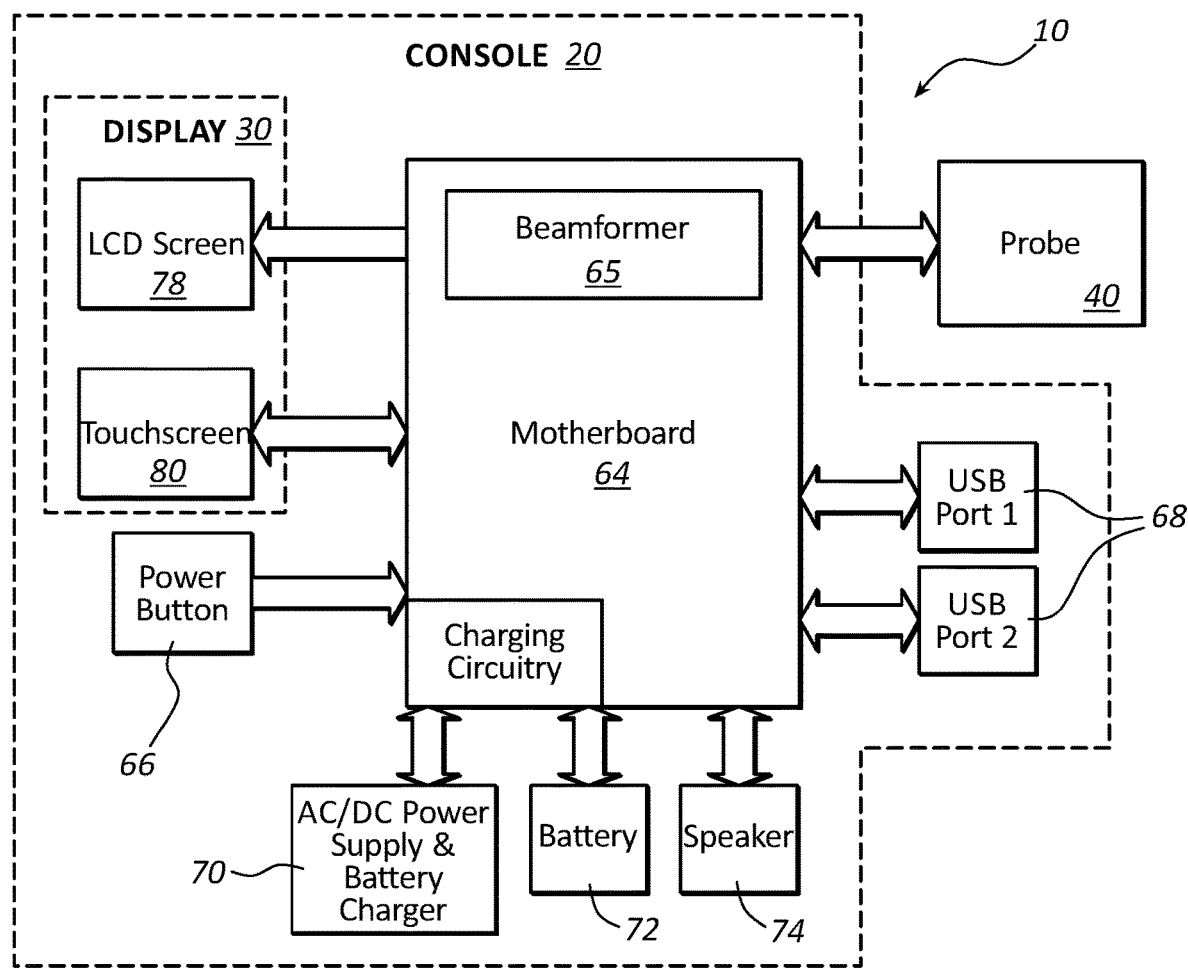
FIG. 2 is a block diagram the ultrasound imaging system of FIG. 1.
Figure 4A:
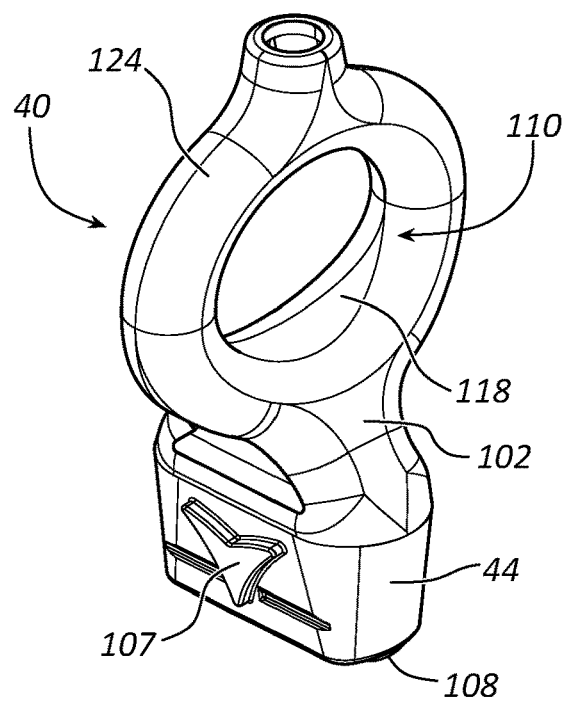
FIGS. 4A-4D are various views of an ultrasound probe according to one embodiment.
Figure 4B:
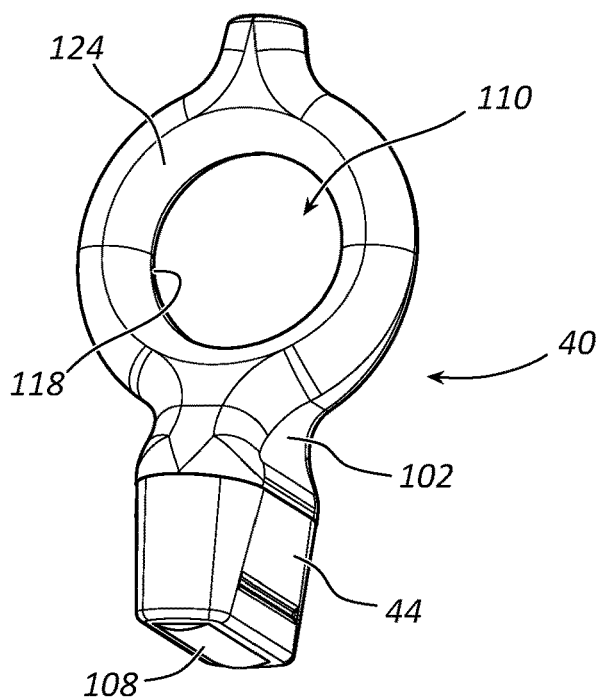
Figure 4C:
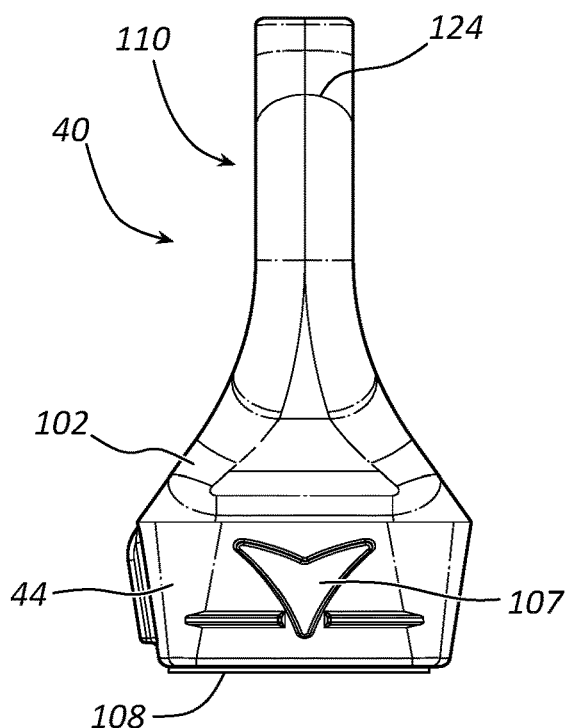
Figure 4D:
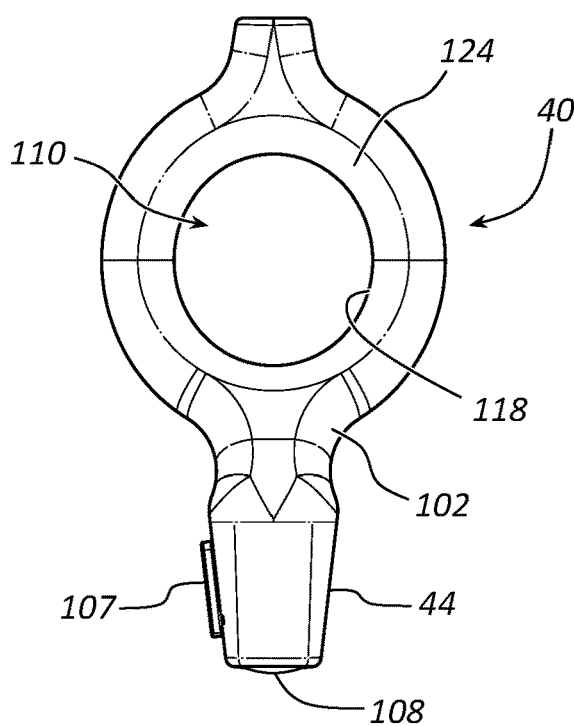
Figure 5A:
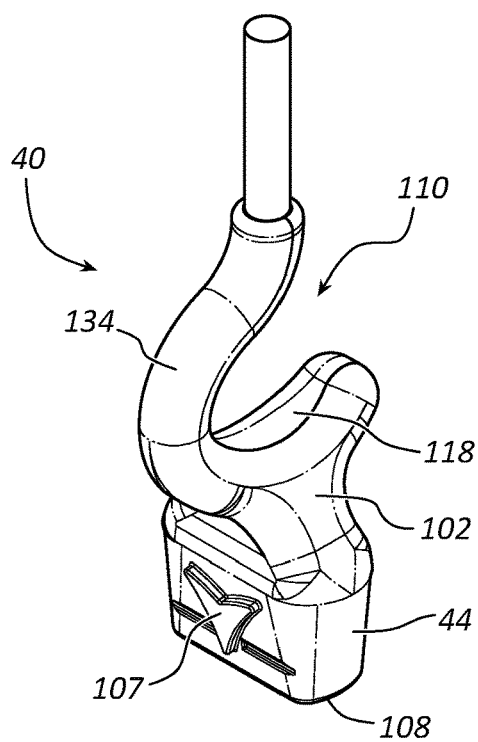
FIG. 5A-5D are various views of an ultrasound probe according to one embodiment.
Figure 5B:
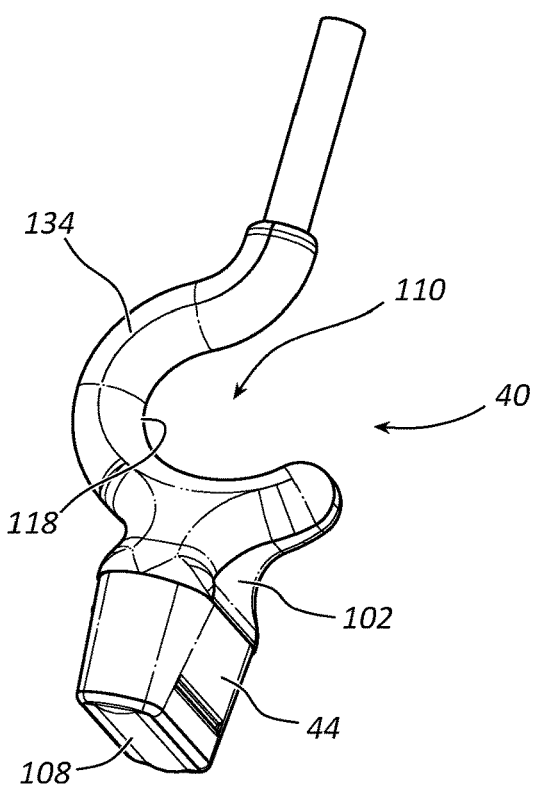
Figure 5C:
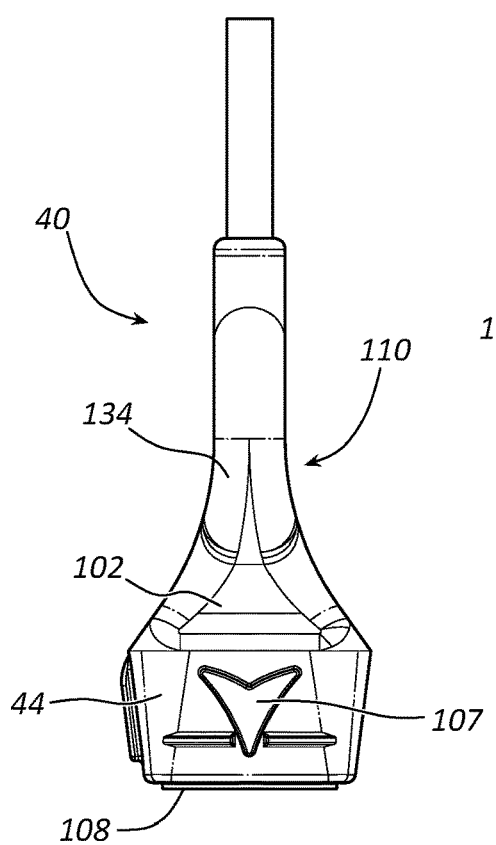
Figure 5D:
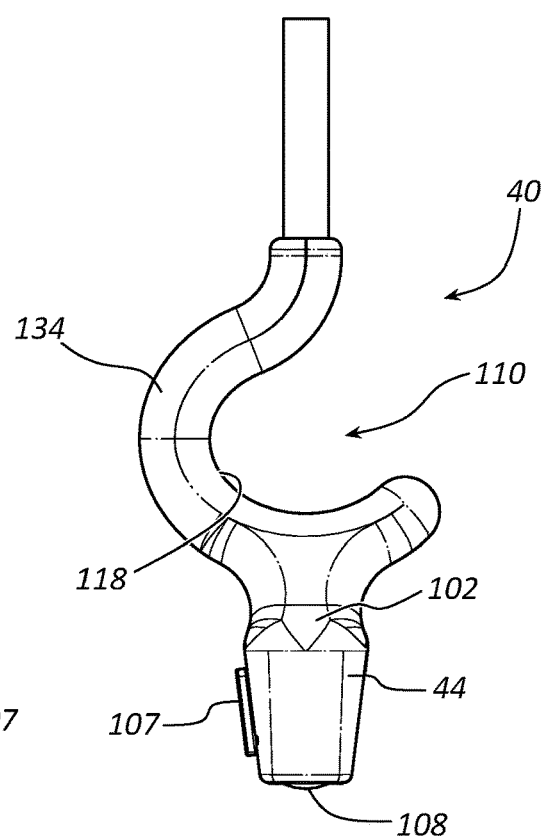
Figure 6A:
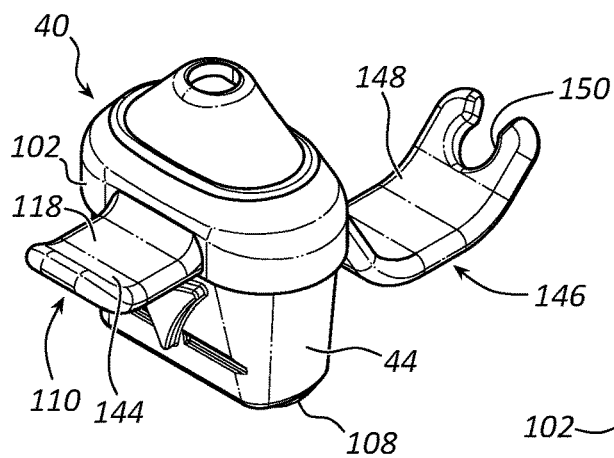
FIGS. 6A-6E are various views of an ultrasound probe according to one embodiment.
Figure 6B:
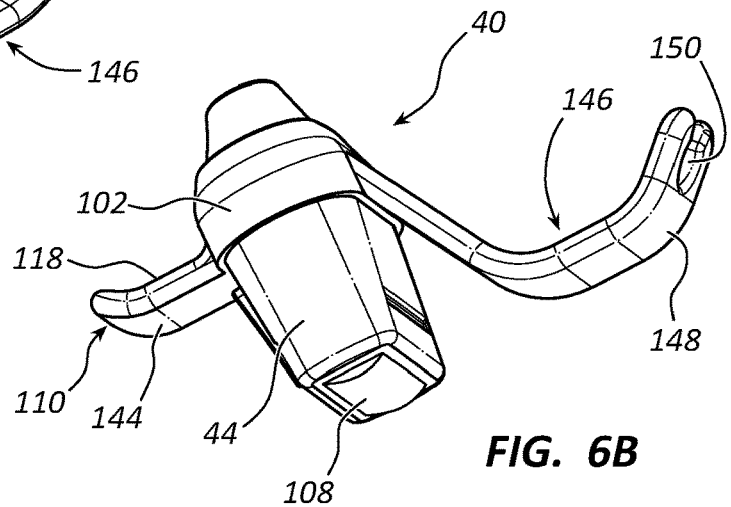
Figure 6C:
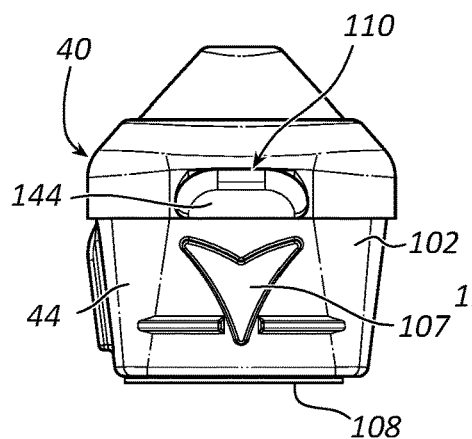
Figure 6D:
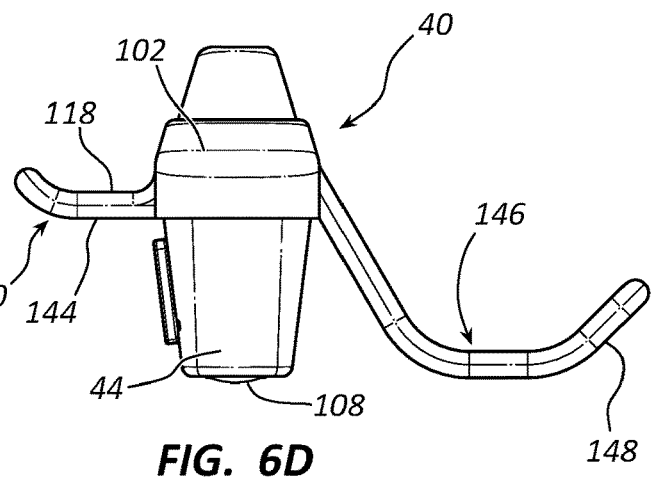
Figure 6E:
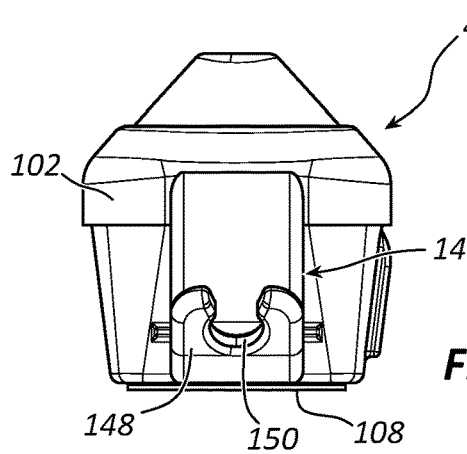

FIG. 2 shows a block diagram of the system 10 of FIG. 1, according to one embodiment. In detail, the console 20, display 30, and probe 40 are represented, as in FIG. 1. The console 20 includes therein a motherboard 64 for governing system functionality and includes a processor or other general or special purpose computer, memory, storage locations, and other components for system operation. A beamformer 65, including suitable circuitry, is also operably included with the motherboard 64 to enable ultrasonic signals to be produced, received, and processed. A power button 66 is included, as are USB ports 68 for interfacing with other devices. An external power supply 70, as well as a battery 72 and speaker 74, are provided for operation. The display 30 in the present embodiment includes an LCD screen 78 or other suitable screen, and a touchscreen 80 to enable touch-based functionality via the display 30. Note that the system 10 can include different, fewer, or more components than those listed here, including those components that enable the system to operate in a networked manner with other local or remote computing or network systems, including for instance, Wi-Fi, Ethernet, Bluetooth, and ZigBee functionality. Also, in addition to a touchscreen, other input modes can also be employed, including a keyboard or mouse input, for instance.

In operation of the system 10, a lens portion of the head 44 of the probe 40 is placed against the skin of the patient so as to ultrasonically image a cross-sectional slice of a vessel, such as a vein, or other internal body tissue of the patient below the surface of the skin. Indeed, a target location of the vessel imaged by the probe 40 is disposed a substantially vertical depth below the end of the probe. The vessel is imaged by the system 10 in preparation for accessing the vessel with a needle in preparation for inserting a catheter into the vessel, in one embodiment. Though shown here as a vessel, the target location can be any one of various subcutaneous locations within the body.

FIGS. 3A-3D depict various features of the probe 40 including the head 44 thereof, in accordance with one embodiment. As shown, the probe 40 includes a body 102 defining lateral surfaces 102A and end surfaces 102B, with the head 44 of the probe defining a distal end of the probe body. A lens 108 is disposed at the distal end of the probe body 102 and is configured to enable passage therethrough of ultrasonic signals. An orientation arrow 107 is included in the illustrated embodiment to assist a user of the imaging system in determining proper needle placement through the skin surface of a patient. A cable 104 is shown extending from a proximal end of the probe body 102 to operably connect the probe to the console 20 (FIG. 1), though the cable can extend from the probe in accordance with various different configurations.

In the present embodiment, the probe 40 includes a finger grip portion 110 configured to enable the user of the probe to grasp, support, and handle the probe with one or more fingers of a single hand of the user while leaving one or more fingers of the user's hand free to be used in other ways. In the present embodiment, the finger grip portion 110 includes two angled, protruding elements 114 extending from the opposing lateral surfaces 120A of the probe body 102. Each of the protruding elements 114 defines, together with a proximate portion of the lateral surface 102A of the probe body 102, a concavely shaped grip surface 118 into which a user's finger is received in order to support and move the probe 40 during imaging system operation.

In the present embodiment, the probe 40 is placed between a forefinger (index finger) and a middle finger of a single hand of the user such that an inside portion of the forefinger engages one of the grip surfaces 118 and an inside portion of the middle finger engages the other grip surface on the opposing side of the probe. In this way, the user is able to lift, maneuver, slide, and otherwise move the probe 40 with only two fingers during operation of the imaging system 10. Note that other fingers of the user's hand can alternatively be used to hold the probe 40. This further enables the remaining three fingers of the user's hand to be employed in other ways during ultrasonic imaging by the probe 40. These other ways include, for instance, applying traction to the skin surface, touching the patient in order to impart comfort, establishing or marking a physical reference point etc.

Note that the engagement of the probe 40 by the hand of the user is such that the user's hand is positioned substantially parallel with respect to the skin surface of the patient, i.e., horizontally, in a typical imaging procedure. This in turn enables the user to move the probe accurately and easily, with relatively small movements across the skin surface, which results in improved imaging results. Note also that the probe body 102 in this and other embodiments includes a suitable material, such as a thermoplastic. In one embodiment, the material includes R-5100 polyphenylsulfone.

Reference is now made to FIGS. 4A-4D, which depict various details of the probe 40 and its finger grip portion 110 for enabling grasping, supporting, and handling of the probe with one or more fingers of a single hand of the user while leaving one or more fingers of the user's hand free to be used in other ways as described herein, according to another embodiment. As shown, the finger grip portion 110 includes a ring 124 defined by the body 102 of the probe 40. The ring 124 is sized in one embodiment to receive a finger of the user, such as the forefinger or middle finger. To that end, an inner annular surface of the ring 124 serves as a grip surface 118 against which the user's finger rests to enable the finger to handle and control movement of the probe 40. It is thus noted that the finger grip portion 110, i.e., the ring 124 in the present embodiment, further serves as one example of a retention portion to retain engagement of the probe 40 with the user's finger(s). Note that, in this and other embodiments, the retention portion enables the probe 40 to remain attached with the finger of the use even when the finger and/or hand of the user is lifted from the skin surface, which enables the user to perform other tasks without putting down the probe.

In one embodiment, the size of the ring 124 can be configured such that the user's finger can be inserted varying distances through the ring in order to encounter a fit suitable for moving and handling the probe 40. As such, the ring 124 can be sized in one or more of varying diameters. In another embodiment, an insert can be removably fitted in to the ring 124 to adjust the size of the ring opening to accommodate differently sized fingers. Note that in one embodiment, all or part of the finger grip portion can be flexible/resilient so as to deform to a user's finger. Note also, that the probe 40 in the embodiment illustrated in FIGS. 4A-4D is about 2.5 inches high, the probe head 44 about 1 inch wide, and the ring 124 about 1.5 inches wide, though other dimensions are possible for this and the other embodiments described herein.

Figure 17:
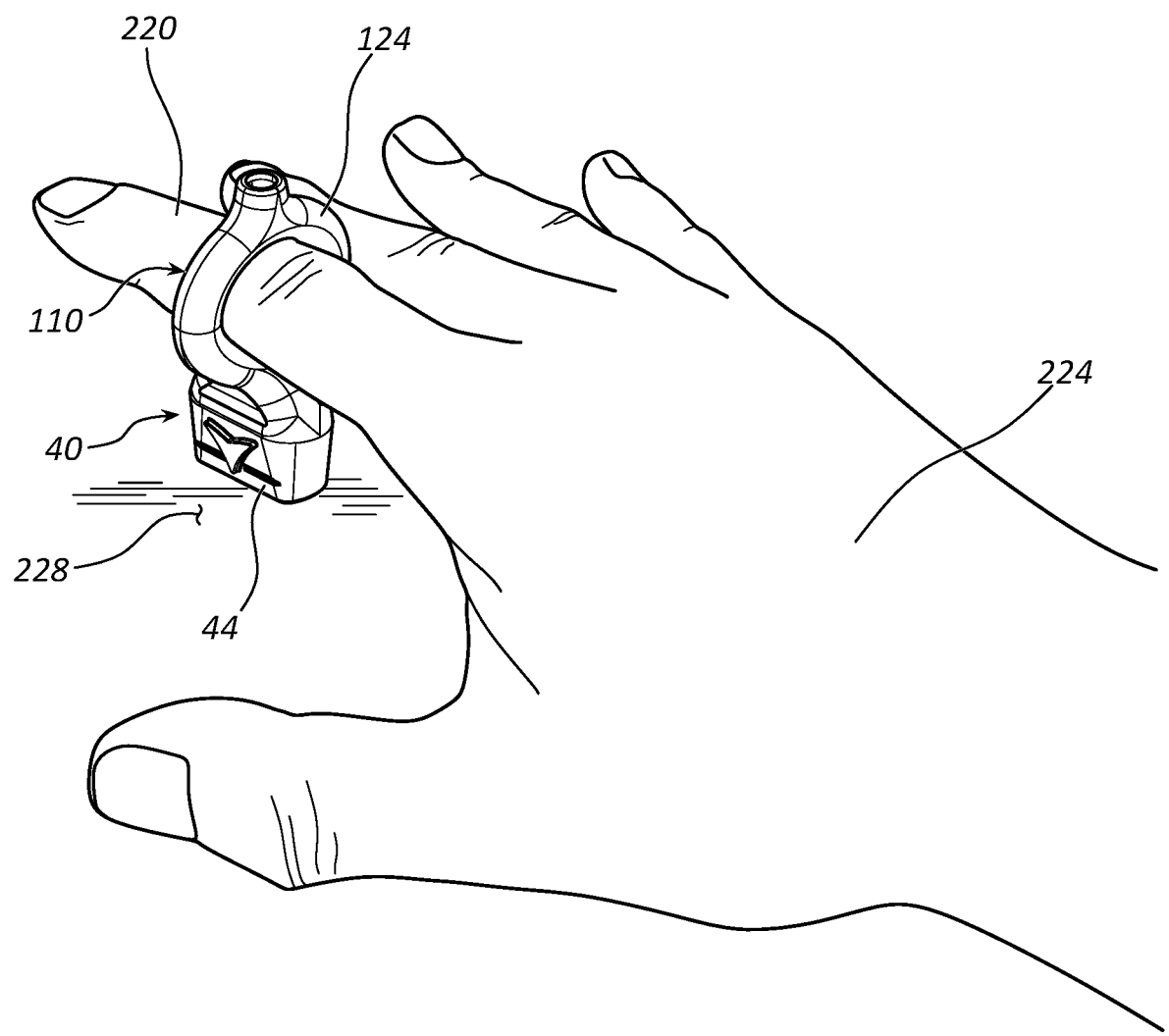
FIG. 17 is a perspective view showing the hand of a user engaged with an ultrasound probe.

FIG. 17 shows the probe 40 of FIGS. 4A-4D engaged with a forefinger 220 of a hand 224 of a user in one use embodiment. As shown, the finger grip portion 110, i.e., the ring 124, enables the user's finger to be positioned substantially co-linearly above and in a spaced-apart relationship with respect to the lens 108 of the probe head 44 when the probe is in an operable position on a horizontal skin surface of the patient 228. This enables the user to impart relatively fine amounts of pressure, or traction, to the skin surface via pressing down the probe 40 thereon, and provides enhanced control over the probe. Also shown in FIG. 17 is the manner in which the hand of the user is positioned substantially parallel with respect to the skin surface of the patient, i.e., horizontally, in a typical imaging procedure. As mentioned, this enables the user to move the probe accurately and easily, with relatively small movements across the skin surface, which results in improved imaging results.

Reference is now made to FIGS. 5A-5D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment. As shown, the finger grip portion 110 includes a hook 134 defined by the body 102 of the probe 40. The hook 134 is approximately C-shaped and is sized in one embodiment to receive a finger of the user, such as the forefinger or middle finger, while enabling an opening for ease of finger insertion/removal. An inner surface of the hook 134 serves as the grip surface 118 against which the user's finger rests to enable the finger to handle and control movement of the probe 40. It is thus noted that the finger grip portion 110, i.e., the hook 134 in the present embodiment, further serves as one example of a retention portion to retain engagement of the probe 40 with the user's finger(s).

In one embodiment, the size of the hook 134 can be configured such that different portions of the user's finger can be inserted into the hook in order to encounter a fit suitable for moving and handling the probe 40. As such, the hook 134 can be sized in one or more of varying sizes. In another embodiment, an insert can be removably fitted in to the hook 134 to adjust the size thereof to accommodate differently sized fingers.

The finger grip portion 110, i.e., the hook 134 in the embodiment of FIGS. 5A-5D, enables the user's finger to be positioned substantially co-linearly above and in a spaced-apart relationship with respect to the lens 108 of the probe head 44. This enables the user to impart relatively fine amounts of pressure, or traction, to the skin surface via pressing down the probe 40 thereon, and provides enhanced control over the probe.

Reference is now made to FIGS. 6A-6E, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment. As shown, the finger grip portion 110 includes a tab 144 extending from one of the lateral surfaces 102A of the probe body 102. A terminal portion of the tab 144 includes an upwardly angled lip so as to provide the grip surface 118 on which a finger of the user, such as the forefinger, can rest. Another finger, such as the middle finger on the same hand of the user, can engage the opposing lateral surface 102A of the probe body 102 to enable the two fingers to handle and control movement of the probe 40. Note that other fingers can be employed to grasp the probe 40, as with the other embodiments herein.

The probe 40 of the embodiment of FIGS. 6A-6E further includes a stabilizing portion 146 configured to maintain the probe in an upright, usable position on the skin surface of the patient even when the user's hand is not contacting the probe. In the present embodiment, the stabilizing portion 146 includes an angled leg 148 extending from the lateral surface 102A opposite the tab 144, best seen in FIG. 6D. The leg 148 extends downward (from the perspective shown in FIG. 6D) so as to provide a lower surface substantially flush with the lens 108 of the probe head 44. In this way, the leg 148 stabilizes the probe 40 by providing a second contacting surface for the skin, in addition to the lens 108. Note that the stabilizing portion 146 can also enable the probe 40 to be manipulated by a single finger, in one embodiment. A terminal free end of the leg 148 defines a notch 150, in the present embodiment, the notch configured for removably holding a portion of the cable 104 to keep it away from the hand of the user during use of the probe 40.

Reference is now made to FIGS. 7A-7D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment. As shown, the finger grip portion 110 includes a cylindrical ring 154 extending from the main body 102 of the probe 40. The cylindrical ring 154 is sized in one embodiment to receive a finger of the user, such as the forefinger or middle finger. To that end, an inner cylindrical surface of the ring 154 serves as the grip surface 118 against which the user's finger rests to enable the finger to handle and control movement of the probe 40. It is thus noted that the finger grip portion 110, i.e., the cylindrical ring 154 in the present embodiment, further serves as one example of a retention portion to retain engagement of the probe 40 with the user's finger(s).

In one embodiment, the size of the cylindrical ring 154 can be configured such that the user's finger can be inserted varying distances through the ring in order to encounter a fit suitable for moving and handling the probe 40. As such, the cylindrical ring 154 can be sized in one or more of varying diameters. In another embodiment, an insert can be removably fitted in to the cylindrical ring 154 to adjust the size of the ring opening to accommodate differently sized fingers. In yet another embodiment, the cylindrical ring 154 can have a varying diameter, such as being relatively wider at either end, so as to introduce freedom of movement for a finger inserted therein.

The probe 40 of the embodiment of FIGS. 7A-7D further includes the stabilizing portion 146 configured to maintain the probe in an upright, usable position on the skin surface of the patient even when the user's hand is not contacting the probe. In the present embodiment, the stabilizing portion 146 includes the cylindrical ring 154 itself, best seen in FIG. 7D. The cylindrical ring 154 extends downward (from the perspective shown in FIG. 7D) so as to provide a lower surface substantially flush with the lens 108 of the probe head 44. In this way, the bottom portion of the cylindrical ring 154 stabilizes the probe 40 by providing a second contacting surface for the skin, in addition to the lens 108.

Reference is now made to FIGS. 8A-8D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment.

As shown, the finger grip portion 110 includes the cylindrical ring 124 extending from the body 102 of the probe 40. The cylindrical ring 154 is sized in one embodiment to receive a finger of the user, such as the forefinger or middle finger. To that end, an inner cylindrical surface of the cylindrical ring 154 serves as the grip surface 118 against which the user's finger rests to enable the finger to handle and control movement of the probe 40. It is thus noted that the finger grip portion 110, i.e., the cylindrical ring 154 in the present embodiment, further serves as one example of a retention portion to retain engagement of the probe 40 with the user's finger(s).

In one embodiment, the size of the cylindrical ring 154 can be configured such that the user's finger can be inserted varying distances through the ring in order to encounter a fit suitable for moving and handling the probe 40. As such, the cylindrical ring 154 can be sized in one or more of varying diameters. In another embodiment, an insert can be removably fitted in to the cylindrical ring 154 to adjust the size of the ring opening to accommodate differently sized fingers.

The finger grip portion 110, i.e., the cylindrical ring 154 in the embodiment of FIGS. 8A-8D, enables the user's finger to be positioned substantially co-linearly above and in a spaced-apart relationship with respect to the lens 108 of the probe head 44. This enables the user to impart relatively fine amounts of pressure, or traction, to the skin surface via pressing down the probe 40 thereon, and provides enhanced control over the probe.

Figure 8A:
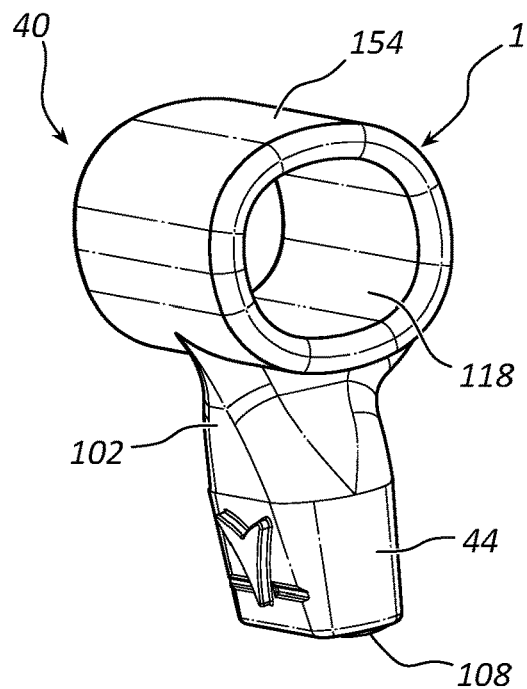
FIGS. 8A-8D are various views of an ultrasound probe according to one embodiment.
Figure 8B:
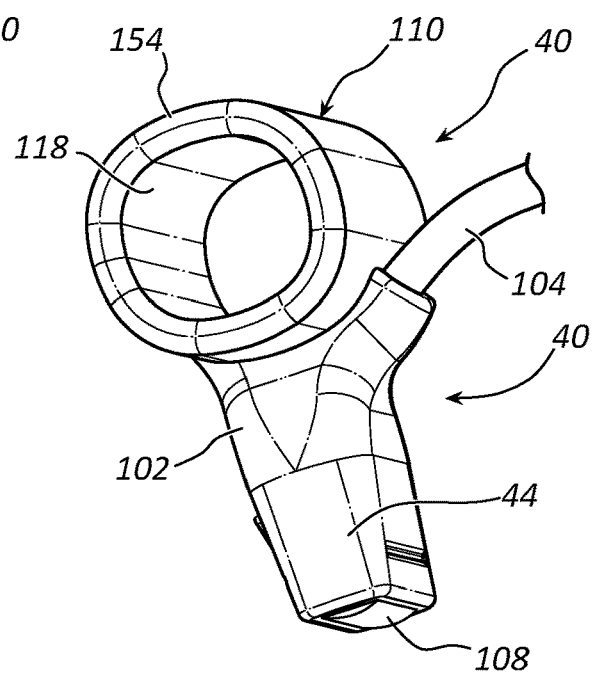
Figure 8C:
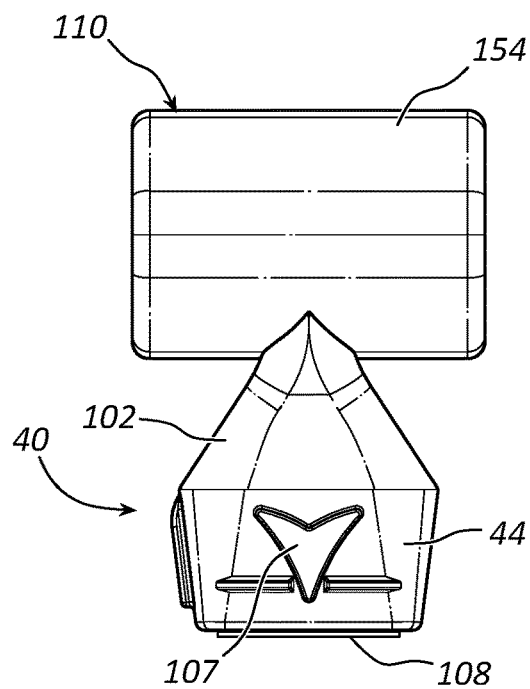
Figure 8D:
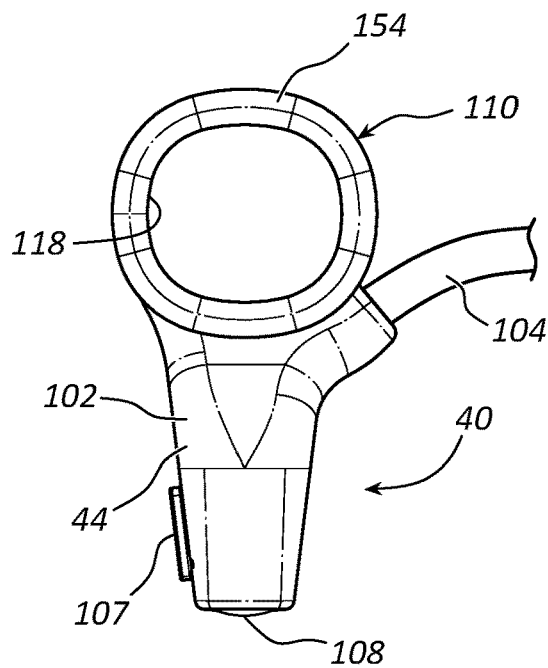
Figure 9A:
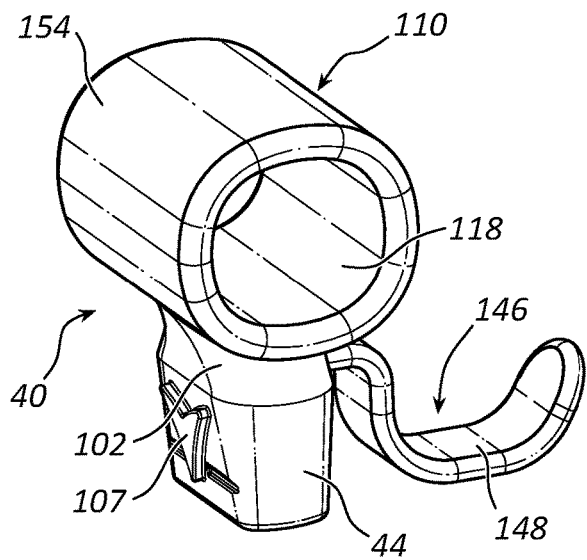
FIGS. 9A-9D are various views of an ultrasound probe according to one embodiment.
Figure 9B:
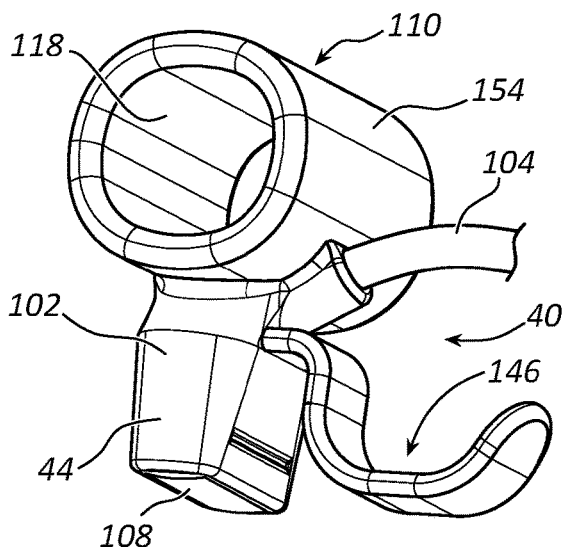
Figure 9C:
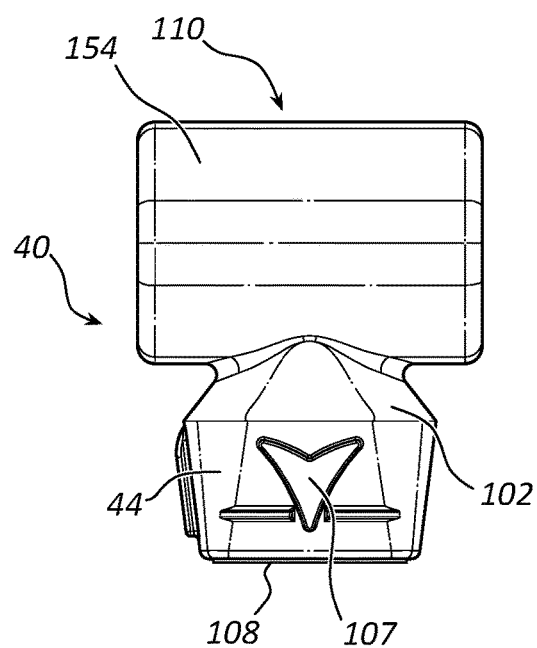
Figure 9D:
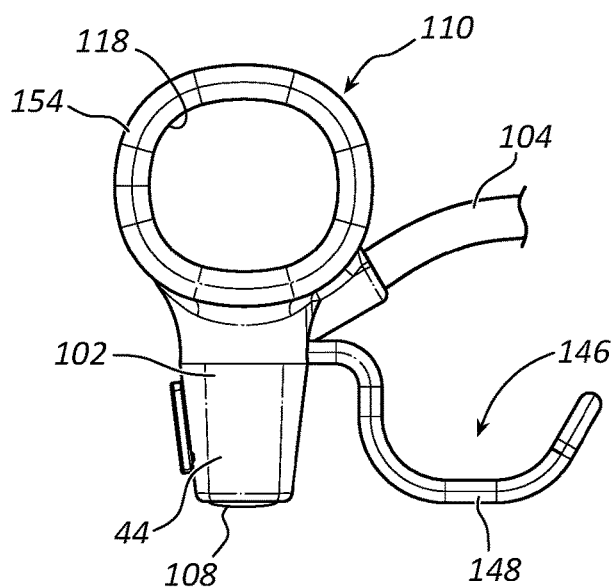
Figure 10A:
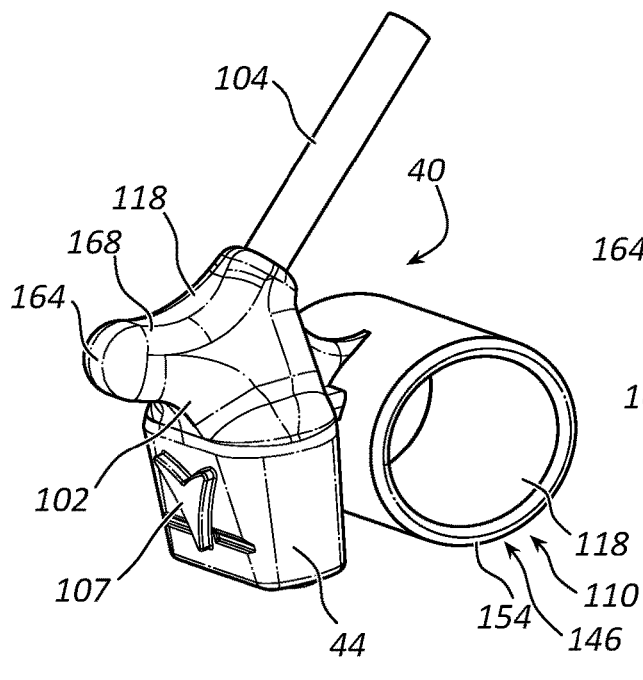
FIGS. 10A-10D are various views of an ultrasound probe according to one embodiment.
Figure 10B:
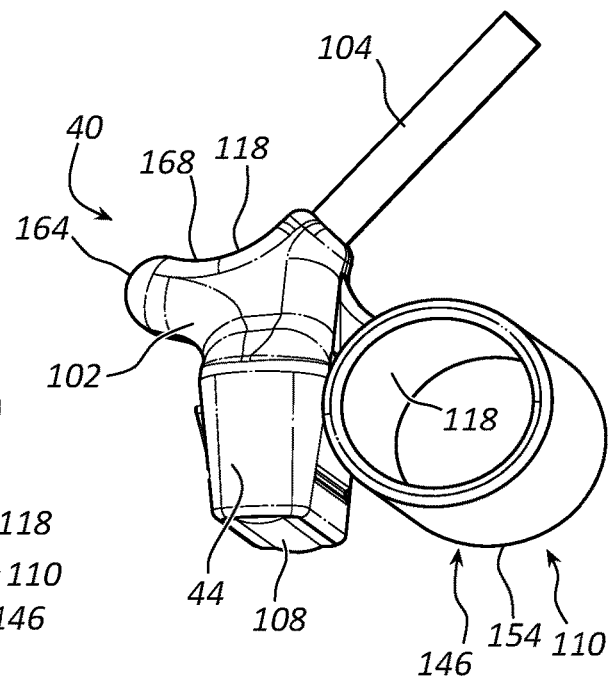
Figure 10C:
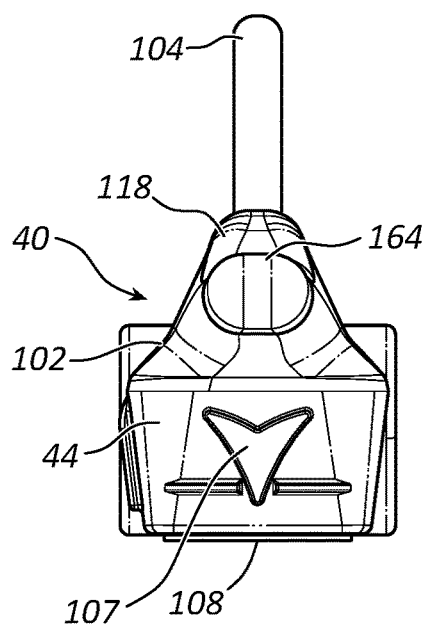
Figure 10D:
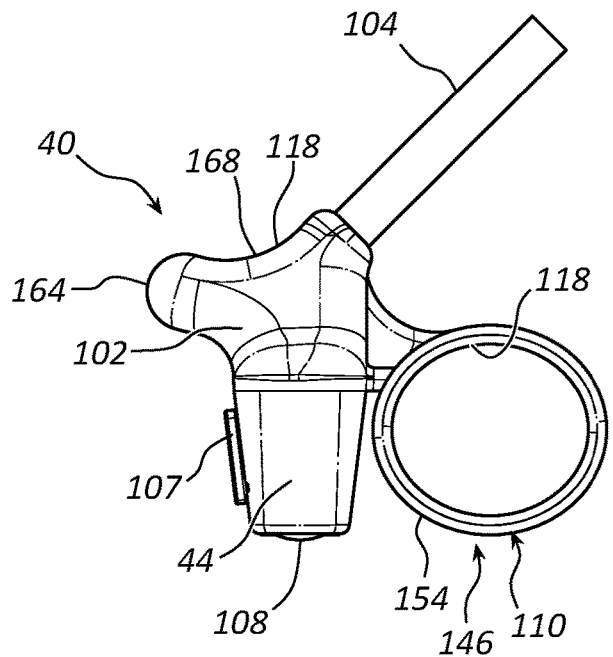
Figure 12A:
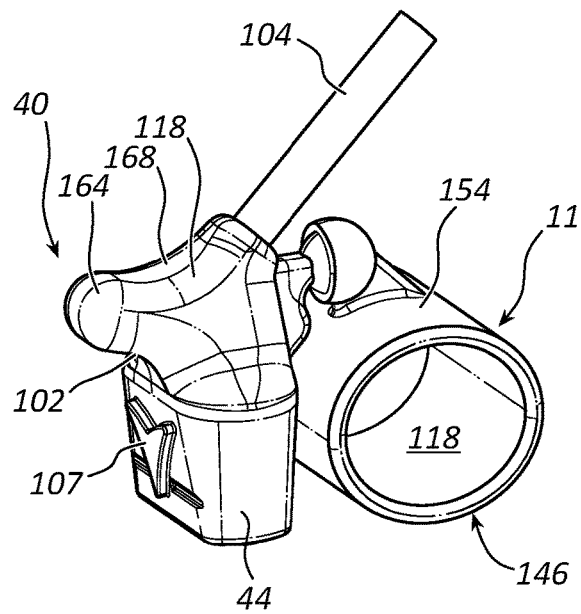
FIGS. 12A-12D are various views of an ultrasound probe according to one embodiment.
Figure 12B:
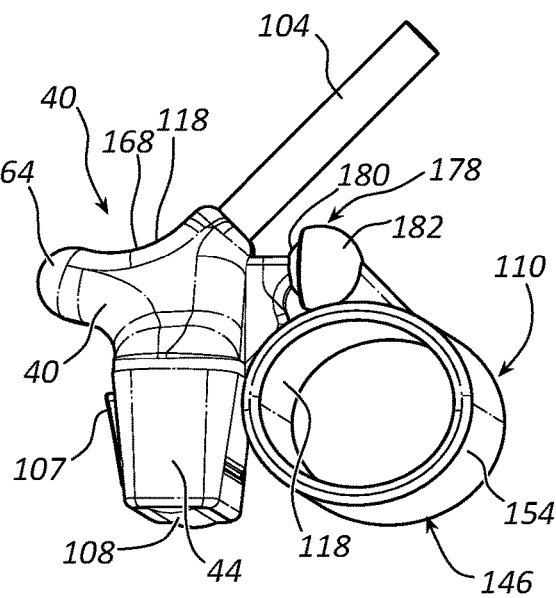
Figure 12C:
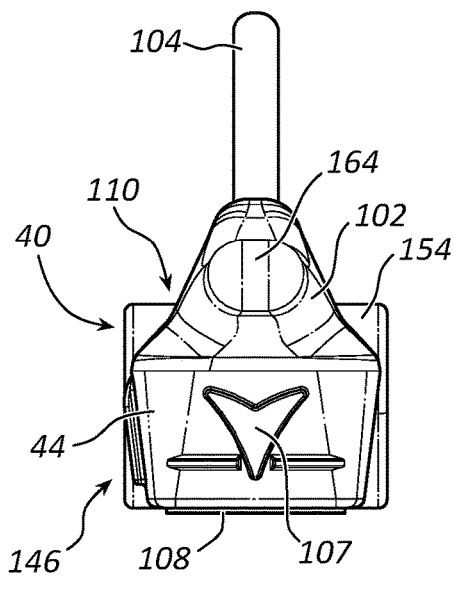
Figure 12D:
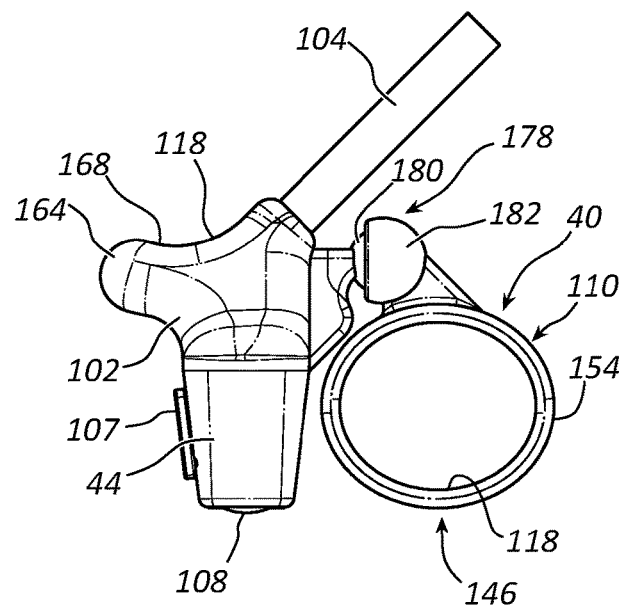

Note in the present embodiment that the cable 104, which operably connects the probe 40 to the console 20 (FIG. 1), extends from the probe body 102 at an angle from the use position of the probe (i.e., from the perspective shown in FIG. 8D). This cable configuration can reduce torque on the probe 40 by the cable 104 as well as keep the cable clear of the user's hand. Such a configuration can be included in other of the embodiments described herein.

Reference is now made to FIGS. 9A-9D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment.

As shown, the embodiment of FIGS. 9A-9D is similar to that shown in FIGS. 8A-8D, with the addition of the stabilizing portion 146—here, the angled leg 148 similar to that shown in the embodiment of FIGS. 6A-6E. Note that the particular shape of the angled leg 148 of FIGS. 9A-9D differs in shape somewhat from the angled leg of FIGS. 6A-6E, while still being configured to maintain the probe in an upright, usable position on the skin surface of the patient even when the user's hand is not contacting the probe. As before, the angled leg 148 extends downward (from the perspective shown in FIG. 9D) so as to provide a lower surface substantially flush with the lens 108 of the probe head 44. In this way, the leg 148 stabilizes the probe 40 by providing a second contacting surface for the skin, in addition to the lens 108.

Reference is now made to FIGS. 10A-10D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment. As shown, the finger grip portion 110 includes a cylindrical ring 154 extending from the main body 102 of the probe 40. The cylindrical ring 154 is sized in one embodiment to receive a first finger of the user, such as the middle finger. To that end, an inner cylindrical surface of the ring 154 serves as the grip surface 118 against which the user's finger rests to enable the finger to handle and control movement of the probe 40. It is thus noted that the finger grip portion 110, i.e., the cylindrical ring 154 in the present embodiment, further serves as one example of a retention portion to retain engagement of the probe 40 with the user's finger(s).

In one embodiment, the size of the cylindrical ring 154 can be configured such that the user's finger can be inserted varying distances through the ring in order to encounter a fit suitable for moving and handling the probe 40. As such, the cylindrical ring 154 can be sized in one or more of varying diameters. In another embodiment, an insert can be removably fitted in to the cylindrical ring 154 to adjust the size of the ring opening to accommodate differently sized fingers.

The probe body 102 further defines a protrusion 164 and a saddle 168 to provide a second grip surface 118 on which a second finger of the user's hand, such as the forefinger, can rest to further support and handle the probe 40. Thus, two fingers of a user's single hand can be employed in the present embodiment to support and use the probe 40. The saddle 168 enables the user's finger to be positioned substantially co-linearly above and in a spaced-apart relationship with respect to the lens 108 of the probe head 44. This enables the user to impart relatively fine amounts of pressure, or traction, to the skin surface via pressing down the probe 40 thereon, and provides enhanced control over the probe.

The probe 40 of the embodiment of FIGS. 10A-10D further includes the stabilizing portion 146 configured to maintain the probe in an upright, usable position on the skin surface of the patient even when the user's hand is not contacting the probe. In the present embodiment, the stabilizing portion 146 includes the cylindrical ring 154 itself, best seen in FIG. 10D. The cylindrical ring 154 extends downward (from the perspective shown in FIG. 10D) so as to provide a lower surface substantially flush with the lens 108 of the probe head 44. In this way, the bottom portion of the cylindrical ring 154 stabilizes the probe 40 by providing a second contacting surface for the skin, in addition to the lens 108.

Reference is now made to FIGS. 11A-11D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment.

As shown, the embodiment of FIGS. 11A-11D is similar to that shown in FIGS. 10A-10D, with the finger grip portion 110 including a cylindrical hook 174 extending from the probe body 102. The cylindrical hook 174 is approximately C-shaped and is sized in one embodiment to receive a finger of the user, such as the forefinger or middle finger, while enabling an opening for ease of finger insertion/removal. An inner surface of the hook 134 serves as the grip surface 118 against which the user's finger rests to enable the finger to handle and control movement of the probe 40. In one embodiment, the cylindrical hook 174 is resilient such that it can deform a limited amount to conform to the size of the user's finger and remain connected therewith. It is thus noted that the finger grip portion 110, i.e., the hook 134 in the present embodiment, further serves as one example of a retention portion to retain engagement of the probe 40 with the user's finger(s).

Note that in one embodiment the cylindrical hook 174 can include an oval cross-sectional shape to further enhance its engagement with the user's finger. In one embodiment, excess material comprising a sterile cover that is draped over the probe 40 can be inserted into the interior portion of the cylindrical hook 174 in order to increases the engagement of the cylindrical hook with the user's finger (and note that this technique can be employed in connection with the other embodiments herein, including those depicted in FIGS. 4A, 5A, 7A, 8A, 9A, 10A, and 12A. In addition, the cylindrical hook 174 in one embodiment can be removable as to enable cylindrical rings or other finger retention portions of different sizes/configurations to be interchanged on the probe 40.

Also, as with the cylindrical ring 154 of the embodiment shown in FIGS. 10A-10D, the cylindrical hook 174 of the present embodiment serves as the stabilizing portion 146, configured to maintain the probe 40 in an upright, usable position on the skin surface of the patient even when the user's hand is not contacting the probe.

Reference is now made to FIGS. 12A-12D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment.

As shown, the embodiment of FIGS. 12A-12D is similar to that shown in FIGS. 10A-10D, with the finger grip portion 110 including the cylindrical ring 154, which further serves as the stabilizing portion 146. The embodiment shown in FIGS. 12A-12D includes an articulating component 178 disposed between the cylindrical ring 154 and the main portion of the probe body 102. In detail, the articulating component 178 includes a ball 180 included on the main portion of the probe body 102 and a corresponding socket 182 included on the cylindrical ring and sized to receive the ball therein so as to enable articulating movement between the probe head 44 and the cylindrical ring 154 through which a user's finger is received during an ultrasound imaging procedure. The articulating component 178 enables relative movement between the probe head 44 and the cylindrical ring, thus enabling freedom of movement of the probe 40. This is useful when it is desired to lift the lens 108 above the skin surface while desiring to keep one or more fingers on the skin surface. Note that other articulating and jointed structures can be employed to provide such relative movement, such as a hinge in one embodiment. Also, the ball and socket configuration can be reversed in position, in one embodiment.

Note that, in the present and previous embodiments discussed above, the probe head 44, lens 108, and orientation arrow 107 are configured similar to standard probe heads so as to lend familiarity to the user in terms of placement of the probe head and lens on the skin surface and inserting needles, etc.

Reference is now made to FIGS. 13A-13D, which depict various details of the probe 40 and its finger grip portion 110 for enabling grasping, supporting, and handling of the probe with one or more fingers of a single hand of the user while leaving one or more fingers of the user's hand free to be used in other ways, according to another embodiment. As shown, the probe body 102 includes a top disk 186 and a bottom disk 188 that are separated by the finger grip portion 110, here configured as an hourglass-shaped surface 184 that defines the grip surface 118. Two fingers of a user's single hand, such as the forefinger and middle finger (though other digits could be used), can straddle the hourglass-shaped surface 184 to grasp and handle the probe 40. A flat side surface 190 is included on the bottom disk 188 proximate the lens 108, which is disposed on the bottom of the probe head 44, from the perspective shown in FIGS. 13C and 13D. A cable can extend from a cable conduit 194 at a top surface of the probe body 102. As in previous embodiments, the probe body design shown in the present embodiment enables a finger to be positioned substantially directly over the lens 108 in a spaced-apart arrangement. Note that the flat bottom surface of the bottom disk 188, best seen in FIG. 13B, serves as a stabilizing portion in the present embodiment for enabling the probe 40 to rest without assistance on the skin surface of the patient.

Figure 14:
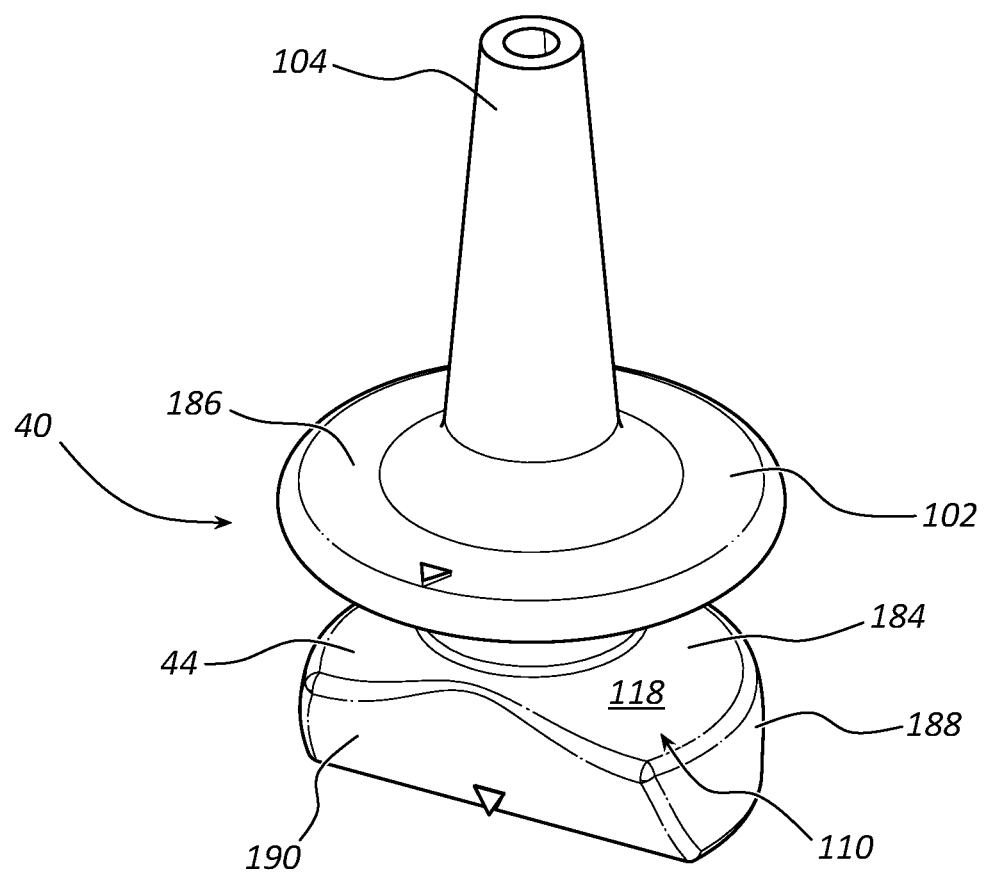
FIG. 14 is a perspective view of an ultrasound probe according to one embodiment.

FIG. 14 depicts the probe 40 according to one embodiment. The probe 40 here is similar to that shown in the embodiment of FIGS. 13A-13D, but with the flat side surface 190, proximate the lens 108, being relatively larger.

Figure 15A:
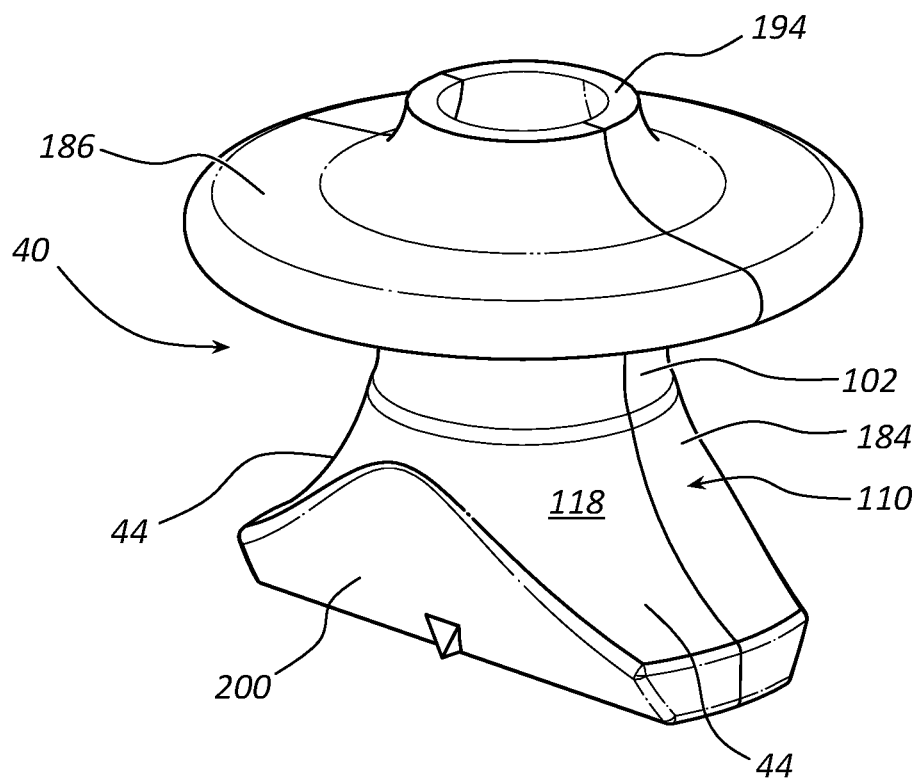
FIGS. 15A and 15B are various views of an ultrasound probe according to one embodiment.
Figure 15B:
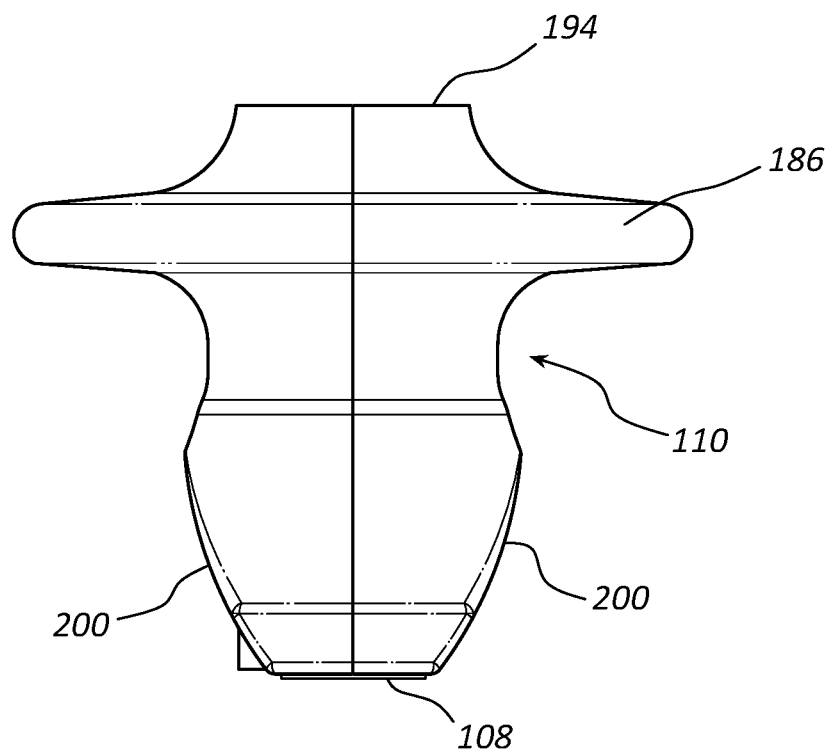
Figure 16A:
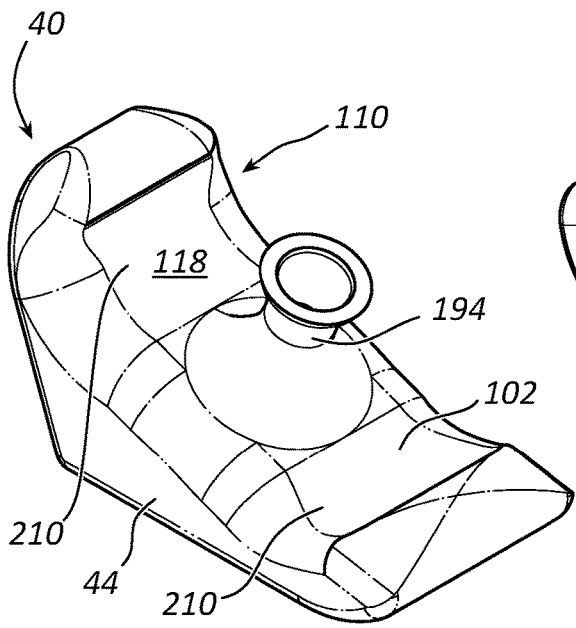
FIGS. 16A-16D are various views of an ultrasound probe according to one embodiment.
Figure 16B:
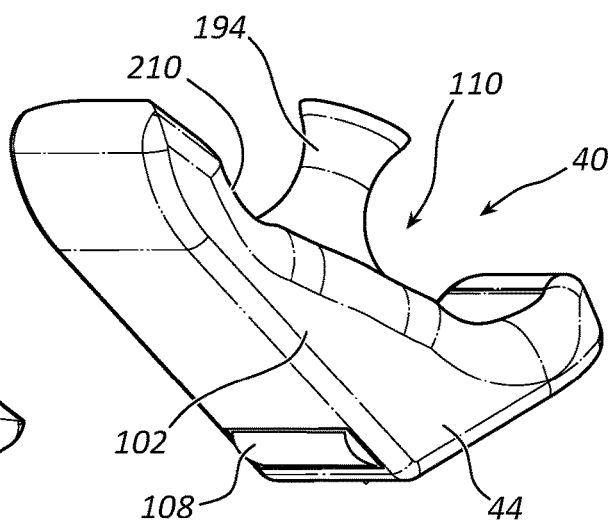
Figure 16C:
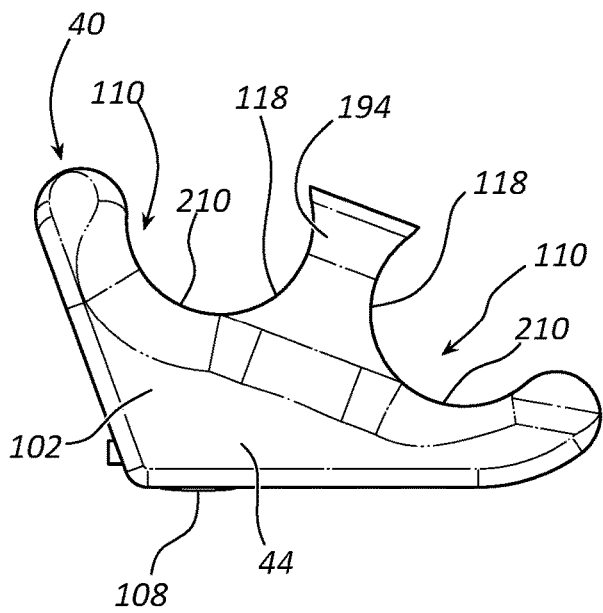
Figure 16D:
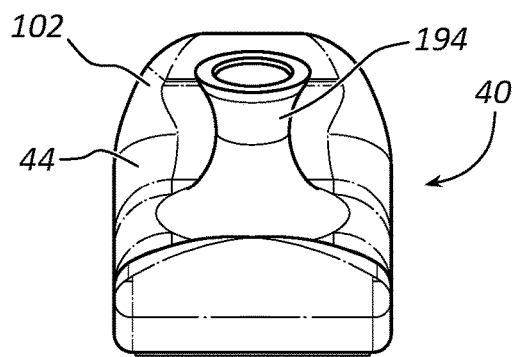

FIGS. 15A and 15B depict yet another variation of the embodiment shown in FIGS. 13A-13D, wherein the bottom disk of the probe body 102 is omitted and two chamfered surfaces 200 are defined on a bottom portion of the probe body proximate the lens 108. These and other variations to the probe body 102 while still enabling grasping and handling of the probe 40 with one or more fingers but while still enabling other fingers of the user's hand to be free for other purposes, are therefore contemplated.

FIGS. 16A-16D depict various details of the probe 40 and its finger grip portion 110 for enabling grasping, supporting, and handling of the probe with one or more fingers of a single hand of the user while leaving one or more fingers of the user's hand free to be used in other ways, according to another embodiment. As shown, the probe body 102 includes a generally wedge-shaped configuration, with the lens 108 of the probe head 44 disposed on a bottom surface thereof, from the perspective shown in FIGS. 16C and 16D. Note that the flat bottom surface of the probe body 102, best seen in FIG. 16B, serves as a stabilizing portion in the present embodiment for enabling the probe 40 to rest without assistance on the skin surface of the patient.

The cable conduit 194 extends from the probe body 102 and two finger grip portions 110 are included, namely, two channels 210 that are defined by the body and are disposed adjacent the coble conduit so as to provide two concavely shaped grip surfaces 118. Two fingers of a single hand of the user, such as the forefinger and middle finger, can be received into the channel 210 to support and handle the probe 40, while enabling other fingers of the user's hand to be used for other purposes. These and other probe body shapes and finger grip portion configurations are therefore contemplated.

Note that the probes discussed herein are further configured to enable a sterile cover to be thereover and for elastic bands to be used to secure the cover to the probe. The probes herein are also configured to be symmetrical along at least one midline axis so as to enable both left-handed and right-handed use.

In one embodiment, it is appreciated that icons/symbols may be placed on the probe body 102 to assist a user in knowing where to place finger(s) for use of the probe 40.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An ultrasound probe, comprising:
   a body;
   a lens included on a head portion of the body through which ultrasound signals can be passed, the lens providing a first skin contact surface for the ultrasound probe;
   a stabilizing portion extending from the body, the stabilizing portion having a bottom surface adjacent a skin surface of a patient when the lens is placed on the skin surface, the bottom surface of the stabilizing portion providing a second skin contact surface for the ultrasound probe;
   an articulating component interposed between the body and the stabilizing portion; and
   a finger grip portion configured to enable a user of the ultrasound probe to grasp and maneuver the ultrasound probe during use thereof with no more than two fingers on a single hand of the user, wherein the stabilizing portion is configured to move across the skin surface of the patient along with the finger grip portion.

2. The ultrasound probe as defined in claim 1, wherein the finger grip portion is configured to enable the user to grasp and maneuver the ultrasound probe with a single finger.

3. The ultrasound probe as defined in claim 1, wherein the finger grip portion and the stabilizing portion are included in a singular structure.

4. The ultrasound probe as defined in claim 1, wherein the finger grip portion includes at least one of a ring structure and a C-shaped structure.

5. The ultrasound probe as defined in claim 4, wherein the stabilizing portion includes an arm extending from the body of the ultrasound probe.

6. The ultrasound probe as defined in claim 4, wherein the stabilizing portion is included with the ring structure.

7. The ultrasound probe as defined in claim 4, wherein the ring structure defines a cylindrical ring.

8. The ultrasound probe as defined in claim 7, wherein the finger grip portion further includes a saddle portion configured to receive a finger thereon.

9. The ultrasound probe as defined in claim 1, wherein the finger grip portion is disposed co-linearly above the lens in a spaced-apart configuration when the ultrasound probe is positioned on the skin surface of the patient.

10. The ultrasound probe as defined in claim 1, wherein the finger grip portion includes a tab extending from the body of the ultrasound probe and the stabilizing portion includes an angled arm extending from the body of the ultrasound probe.

11. The ultrasound probe as defined in claim 1, wherein the finger grip portion is configured to be engaged by at least one of a forefinger and a middle finger of the hand of the user.

12. The ultrasound probe as defined in claim 1, wherein at least a thumb and a finger of the hand of the user are configured to be free to use when the hand of the user is grasping the ultrasound probe.

13. The ultrasound probe as defined in claim 1, wherein the articulating component includes a ball and socket configuration.

14. The ultrasound probe as defined in claim 1, wherein the bottom surface of the stabilizing portion is proximate the lens.

15. The ultrasound probe as defined in claim 14, wherein the finger grip portion includes an hourglass-shaped surface bounded by a top disk and a bottom disk, wherein the hourglass-shaped surface, the top disk, and the bottom disk are defined by the body of the ultrasound probe.

16. The ultrasound probe as defined in claim 14, wherein the finger grip portion includes first and second concave channels defined by the body of the ultrasound probe, the ultrasound probe defining a wedge shape.

17. The ultrasound probe as defined in claim 1, wherein the stabilizing portion includes a notch configured for receiving a cable of the ultrasound probe.

18. The ultrasound probe as defined in claim 1, wherein the finger grip portion is configured to enable the hand of the user to be positioned parallel with respect to the skin surface of the patient.

19. An ultrasound imaging system, comprising:
   a console;
   a display included with the console; and
   the ultrasound probe as defined in claim 1.

* * * * *